US005998596A

United States Patent [19]
Bergan et al.

[11] Patent Number: 5,998,596
[45] Date of Patent: *Dec. 7, 1999

[54] INHIBITION OF PROTEIN KINASE ACTIVITY BY APTAMERIC ACTION OF OLIGONUCLEOTIDES

[75] Inventors: Raymond Bergan, Rockville; Len Neckers, Bethesda, both of Md.

[73] Assignee: The United States of America as represented by the Department of Health and Human Services, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/416,214

[22] Filed: Apr. 4, 1995

[51] Int. Cl.$^6$ .......................... C07H 19/00; C07H 21/02; C07H 21/04; C12N 15/00
[52] U.S. Cl. ...................... 536/22.1; 536/23.1; 536/24.3; 935/76; 935/77; 935/78
[58] Field of Search ................................. 536/22.1, 23.1, 536/24.1, 24.3; 514/44

[56] References Cited

U.S. PATENT DOCUMENTS

| | | | |
|---|---|---|---|
| 5,194,599 | 3/1993 | Froehler et al. | 536/26.72 |
| 5,256,775 | 10/1993 | Froehler et al. | 536/25.6 |
| 5,264,562 | 11/1993 | Matteucci | 536/23.1 |
| 5,582,981 | 12/1996 | Toole et al. | 435/6 |
| 5,629,147 | 5/1997 | Asgari et al. | 435/5 |

FOREIGN PATENT DOCUMENTS

| | | | |
|---|---|---|---|
| WO9214843 | 9/1992 | WIPO | C12Q 1/68 |
| WO9402646 | 2/1994 | WIPO . | |
| WO9404548 | 3/1994 | WIPO | C07H 21/00 |
| WO9406811 | 3/1994 | WIPO | C07H 19/00 |

OTHER PUBLICATIONS

Shah et al., Molecular and Cellular Biology 11(4): 1854–1860 (1991).
Shtivelman et al., Cell 47(2): 277–284 (1986).
Shtivelman et al., Nature 315 :550–554 (1985).
The Boehringer Mannheim Biochemicals Catalog, 1990–91 Edition, pp. 139–140 and 226–227.
Gerkin et al. Genbank Accession No.: L18690 submitted to Genbank on May 27, 1993.
Peles et al., EMBO 10 (8): 2077–2086 (1991).
The Boehringer Mannheim Biochemicals Catalog, 1990–91 Edition, pp. 226–227.
Shtivelman et al. Cell 47: 277–284 (1986).
Bergan et al. Nucleic Acids Research 22(11): 2150–2154 (1994).
Wang et al. Biochemistry 32: 1899–1904 (1993).
Paborsky et al. The Journal of Biological Chemistry 268 (28): 20,808–20,811 (1993).
Conrad et al. The Journal of Biological Chemistry 269(51):32,051–32,054 (Dec. 1994).
Darnell et al. "Molecular Cell Biology", pp. 110–114 Scientific American Books New York, NY (1986).
Bergan et al, Aptameric Inhibition of $p210^{bcr-abl}$ Tyrosine Kinase Autophosphorylation by Oligodeoxynucleotides of Defined Sequence and Backbone Structure, *Nucleic Acids Research*, 1994, vol. 22, No. 11, pp. 2150–2154.
Bergan et al, Synthetic Oligonucleotides: Potent Aptameric Inhibitors of Protein Tyrosine Kinases, *J. of Biochemistry*, Mar. 29, 1993, Keystone Symposium, Abstract S400, p. 210.
Gao et al, Inhibition of Herpes Simplex Virus Type 2 Growth by Phosphorothioate Oligodeoxynucleotides, *Antimicrobial Agents and Chemotherapy*, May 1990, vol. 34, No. 5, pp. 808–812.
Marshall et al, Phosphorodithioate DNA as a Potential Therapeutic Drug, *Science*, vol. 259, Mar. 12, 1993, pp. 1564–1570.
Tuerk et al, RNA Pseudoknots That Inhibit Human Immunodeficiency Virus Type 1 Reverse Transcriptase, *Proc. Natl. Acad. Sci. USA*, vol. 89, Aug. 1992, pp. 6988–6992.
Wang et al, The Tertiary Structure of a DNA Aptamer Which Binds to and Inhibits Thrombin Determines Activity, *Biochemistry*, 1993, 32, pp. 11285–11292.
Padmanabhan et al, The Structure of α–Thrombin Inhibited by a 15–mer Single–Stranded DNA Aptamer, *The Journal of Biological Chemistry*, vol. 268, No. 24, Aug. 25, 1993, pp. 17651–17654.
Latham et al, The Application of a Modified Nucleotide in Aptamer Selection: Novel Thrombin Aptamers Containing 5–(1–Pentynyl)–2'–Deoxyuridine, *Nucleic Acids Research*, vol. 22, No. 14, 1994, pp. 2817–2822.
Griffin et al, The Discovery and Charcterization of a Novel Nucleotide–Based Thrombin Inhibitor, *Gene*, vol. 137, No. 1, 1993, pp. 25–31.
Bock et al, Selection of Single–Stranded DNA Molecules That Bind and Inhibit Human Thrombin, *Nature*, vol. 355, Feb. 6, 1992, pp. 564–566.

*Primary Examiner*—W. Gary Jones
*Assistant Examiner*—Ethan Whisenant
*Attorney, Agent, or Firm*—Morgan & Finnegan, L.L.P.

[57] ABSTRACT

The present invention are oligonucleotides that specifically bind to and directly inhibit the biological function of target molecules such as proteins, peptides or derivatives. The direct or aptameric interaction of oligonucleotides of the present invention with proteins, peptides and derivatives represents a non-antisense mediated effect. The oligonucleotides have been shown to bind to isolated target molecules and to inhibit biological function of the target molecule within cells. In particular, the oligonucleotides have been shown to directly inhibit the kinase activity of protein-tyrosine kinase. The oligonucleotides of the present invention have significant beneficial effects against a chronic myelogenous leukemia derived cell line as demonstrated using cellular phosphotyrosine content as well as cellular growth in soft agar.

12 Claims, 10 Drawing Sheets

| lane | contents | sequence |
|---|---|---|
| 1 | MW stds | |
| 2 | control | no OLGN |
| 3 | BCR-AS | GTCCACCATGGCGCGGCCGGC |
| 4 | BCR-SCR | TCCGCGAACCCGGTGCGCCGG |
| 5 | ABL-IbAS | TCCAGGCTGCTGCCCCATAAA |
| 6 | ABL-IbSCR | CCGACCACTTCCGAGTACTAG |
| 7 | B/A-AS | CGCTGAAGTTTTGAACTCTGC |
| 8 | B/A-SCR | TGTACGTCCGGCTTACTAGTA |

# INHIBITION OF PROTEIN KINASE ACTIVITY BY APTAMERIC ACTION OF OLIGONUCLEOTIDES

FIELD OF THE INVENTION

The present invention relates to inhibition of protein kinase activity. More particularly, it relates to aptameric oligonucleotides that specifically bind to and inhibit the action of protein-tyrosine kinases.

BACKGROUND OF THE INVENTION

Antisense inhibition of gene expression, mediated either by plasmid generated antisense RNA or exogenously added synthetic single stranded DNA, is now a widely used experimental technique (41, 42). The use of this technology in clinical medicine is also receiving intense investigation (43, 44, 45, 46). However, as our understanding of the intracellular fate of exogenously added synthetic oligodeoxynucleotides (ODNs) expands, it is becoming clear that these molecules can participate in non-antisense mediated phenomena (34). Among the most unexpected of these is the sequence-specific direct interaction of ODNs with proteins. Such so-called "aptamer" effects are presumably mediated by the formation of ODN-protein complexes whose specificity is determined by both ODN sequence and protein structure.

Protein tyrosine kinases (PTKs) transfer the gamma phosphate of either ATP or GTP to specific tyrosine residues of acceptor proteins (1). These enzymes and their substrate proteins are important mediators of cellular signal transduction and their aberrant function is frequently associated with deregulated growth and neoplasia (2–8). In fact, the first oncogenic protein characterized, isolated from the transforming retrovirus Rous sarcoma virus, was the PTK src (9). Many of the subsequently discovered oncogenes are also PTKs. PTK inhibitors, therefore, may represent an important class of anti-neoplastic agents (10–12). The majority of PTK inhibitors consist of agents that either inhibit nucleotide or tyrosine containing substrate binding, while the remainder effect catalysis by other means (13–14). Since a high degree of homology exists among the nucleotide binding domains of many ATP-utilizing enzymes, existing inhibitors of nucleotide binding lack specificity for particular PTKs, and in some cases cannot distinguish between PTKs and other kinases.

Chronic myelogenous leukemia (CML) cells contain a unique chromosomal translocation, the Philadelphia chromosome, resulting in the expression of a novel PTK, the $p210^{bcr-abl}$ protein (15). This PTK has been directly implicated in the ontogeny and progression of CML (16).

Direct interaction of an oligo-deoxynucleotide (ODN) with a protein has been described (33). Although several 'aptamer' effects have been reported in the literature, the rules governing these interactions are not at all clearly understood (33–37). Techniques have been developed to optimize the process of aptameric ODN selection (35). Such an approach has led to the identification of a specific ODN that inhibits thrombin function (33). Until the present invention, ODNs having a specificity for a particular PTK have not been described in the literature.

SUMMARY OF THE INVENTION

The invention is directed to aptameric oligonucleotides and aptameric modified oligonucleotides comprising at least one binding region capable of binding specifically to an target molecule.

An aspect of the invention is an oligonucleotide and modified oligonucleotides comprising at least one binding region capable of binding specifically to a protein, peptide or derivatives thereof.

Another aspect of the invention is an oligonucleotide and modified oligonucleotides comprising at least one binding region capable of binding specifically to a protein kinase, oncogene protein, or receptor proteins.

An object of the invention is to prevent or inhibit the biological function of a protein, peptide or derivatives thereof using the oligonucleotides or modified oligonucleotides comprising at least one binding region capable of binding specifically to a target molecule.

Another object of the invention is an aptameric oligonucleotide and aptameric modified oligonucleotides that bind to and prevent or inhibit the biological function of a protein kinase.

Another aspect of the invention is a method of inhibiting or preventing the biological function of a target molecule using the aptameric oligonucleotides, aptameric modified oligonucleotides and mixtures thereof in the form of a pharmaceutical composition.

Yet another aspect of the invention is a method to detect the presence or absence of a target molecule in a biological sample suspected of containing the target using the aptameric oligonucleotides and aptameric modified oligonucleotides in which the target is bound by the oligonucleotide forming a complex and the complex is detected.

A further object of the invention is a method of purifying a target molecule comprising binding of a target molecule from a biological sample to an oligonucleotide coupled to a solid support and recovering the isolated target from the solid support.

Another object of the invention is a method of obtaining an oligonucleotide containing at least one binding region that specifically binds a target comprising incubating a target with a mixture of member oligonucleotides under conditions such that the target complexes with some member of the mixture to form oligonucleotide-target complexes, separating the oligonucleotide target complexes from noncomplexed oligonucleotides, recovering and amplifying the oligonucleotides from the complexes to obtain an oligonucleotide which contains at least one binding region that specifically binds the target.

DETAILED DESCRIPTION OF THE INVENTION

Figure 1A:
FIG. 1A Inhibition of $p210^{bcr-abl}$ kinase activity by ODN1. Autoradiograph of immunoprecipitation kinase reactions: lane 1, molecular weight standards; lane 2, no ODN; lane 3 1 µM ODN1.

As used herein the term "oligonucleotide" shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of a purine or pyrimidine bases, or modified purine or pyrimidine bases. The term "nucleoside" will similarly be generic to ribonucleosides, deoxyribonucleosides, or to any other nucleoside which is an N-glycoside of a purine or pyrimidine base, or modified purine or pyrimidine base.

The term "aptamer" as used herein is a single-stranded or double-stranded oligodeoxyribonucleotide, oligoribonucleotide or modified derivatives that specifically binds and alters the biological function of a target molecule. The target molecule is defined as a protein, peptide and derivatives thereof. The aptamer is capable of binding the target molecule under physiological conditions. An aptamer effect is distinguished from an antisense effect in that the aptameric effects are induced by binding to the protein, peptide and derivative thereof and are not induced by interaction or binding under physiological conditions with nucleic acid.

The present invention is an aptameric single-stranded or double-stranded oligonucleotide and derivatives thereof containing at least one binding region capable of binding specifically to a target molecule or target substance. In binding to the target molecule the oligonucleotide of the invention inhibits or prevents the biological function of the target. The target molecule or substance is a protein, peptide and derivatives thereof. The protein or peptide may be intracellular, extracellular or membrane-associated. Also included as target molecules are proteins, peptides and derivatives thereof produced by natural, recombinant or synthetic means. The target molecule that is bound by the aptamer of the present invention is not limited by size. The molecular weight of the target molecule may in general range from about 500 to about 300,000 daltons. Such proteins include but are not limited to toxins, enzymes, cell surface receptors, adhesion proteins, antibodies, cancer-associated gene products, hormones, cytokines and the like. The protein, peptide or derivative thereof is associated directly or indirectly with a disease in a mammal, including humans. The binding of the oligonucleotide of the present invention to the protein, peptide or derivative thereof prevents or inhibits the disease in the mammal by inhibiting or preventing the biological function of the protein, peptide or derivative thereof.

One embodiment of the present invention is an oligonucleotide or mixture of oligonucleotides capable of regulating signal transduction pathways in cells. More specifically, the present invention is a oligonucleotide or mixture of oligonucleotides that specifically and noncompetitively inhibit a kinase associated with growth regulation through a signal transduction pathway. In another embodiment of the present invention the aptamer is an oligonucleotide, preferably a single-stranded oligodeoxynucleotide or combination of oligodeoxynucleotides (ODNs) that specifically bind to and inhibit the enzymatic activity of a kinase. The oligonucleotides of the present invention inhibit enzymatic activity specifically and noncompetitively by binding to the enzyme in a location at least partially distinct from a nucleotide active site. The oligonucleotides and derivatives thereof of the present invention are useful in inhibiting overexpression of oncogenic protein in cells, where such overexpression of the oncogenic protein is associated with development of cancer.

The present invention is an oligonucleotide or mixtures of oligonucleotides that directly and specifically inhibits a protein kinase, preferably a protein tyrosine kinase (PTK), serine/threonine kinases and the like. Tyrosine kinases that are regulated by the oligonucleotides or mixtures thereof include but are not limited to BCR-ABL, ABL, SRC, LCK, epidermal growth factor receptor, platelet-derived growth factor receptor and the like. Serine/threonine kinases that are regulated by the oligonucleotides or mixtures thereof of the present invention include protein kinase C, CAMP-dependent protein kinase A, MyC, phosphorylase kinase, myosin light chain kinase, CD C-2 kinase, MAP kinase and the like.

Overexpression of protein tyrosine kinase genes and the resultant enzymatic overactivity can contribute to deregulation of cell growth and neoplasia. The oligonucleotides of the present invention are particularly useful in specifically blocking the enzymatic activity of a protein tyrosine kinase resulting in more normal regulated cell growth.

The oligonucleotides of the present invention are distinguished from other nucleoside-based PTK inhibitors that are analogs of adenosine. First, the oligonucleotides of the present invention do not bind at the ATP binding site. Kinetic analysis indicates that the oligonucleotides of the present invention noncompetitively inhibit ATP. Second, the oligonucleotides of the present invention require the presence of multiple linked nucleotides (an oligomer) in contrast to the more typical adenosine analogs that consist of a single base. Third, the function of the oligonucleotides of the present invention is dependent upon the sequence of bases. Fourth, the oligonucleotides of the present invention are distinguished from other nucleoside-based PTK inhibitors by the specificity of inhibition of the target.

Preferably the oligonucleotides of the present invention have high binding affinities for the target molecule. In one embodiment the oligonucleotides of the present invention have Ki values in the sub-micromolar range. The oligonucleotides of the present invention may vary in the number of nucleotide residues and may range from about 3 to about 100 nucleotide residues, preferably ranging from about 3 to about 50 nucleotide residues, more preferably ranging from about 3 to about 21 nucleotide residues. In one embodiment the ODN of the present invention has about 21 nucleotide residues.

In one embodiment, the oligonucleotides of the present invention comprise closely spaced repeats of a consensus sequence. In one particular embodiment, the oligonucleotides of the present invention have as part of their sequence at least one or more GGC sequences. Preferably the oligonucleotides of the present invention have closely spaced repeats of the consensus sequence, GGC. By closely spaced is meant GGC sequences that are directly adjacent to each other and GGC sequences that are separated from each other by 1 intervening base or by about 2 to about 15 intervening bases, to as many as 48 intervening bases.

The oligonucleotides of the invention may contain at least one or more modified linking group, sugar residue and/or base.

Bases include not only known purine and pyrimidine bases, i.e., adenine, thymine, cytosine, guanine and uracil, but also other heterocyclic bases which contain protecting groups or have been otherwise modified or derivatized.

By "modified nucleotides" or modified nucleotides" as used herein are intended to include those compounds containing one or more protecting groups such as acyl, isobutyryl, benzoyl, or the like, as well as any of the art. Examples of such modified or derivatized bases include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methyladenine, 1-methylpseudouracil, 1-methylguanine, 1-methylinosine, 2,2-dimethylguanine, 2-methyladenine, 2-ethylguanine, 3-methylcytosine, 5-methylcytosine, N6-methyladenine, 7-methylguanine, 5-methylaminomethyluracil, 5-methoxyaminomethyl-2-thirouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 3(3-amino-3-N-2-carboxypropyl) uracil, and 2,-diaminopurine.

Modified nucleosides or nucleotides can also include modifications on the sugar moiety, for example, wherein one or more of the hydroxyl groups are replaced with halogen or aliphatic groups, or functionalized as ethers, amines, etc.

The oligonucleotides according to the present invention may be of any length, but lengths of about three to about one hundred nucleotides, or about three to about fifty nucleotides or preferably about three to about 21 nucleotides are particularly useful for most applications.

According to the present invention, the 3' end and/or the 5' end of the polynucleotide will contain at least two phosphoramidate internucleotide linkages. The remaining internucleotide linkages may be phosphodiester linkages, phosphorothioate linkages or phosphorodithioate linkages, or any other internucleotide linkage, other than a phosphoramidate, or combinations of these other linkages. Methods for preparing such non-phosphoramidate linkages are known in the art, e.g., as taught by Froehler et al., *Nuc. Acids Res.* 14:5399–5467 (1986), and Froehler, B., *Tet. Lett.* 27:5575–5578 (1986), cited above and incorporated by reference herein.

Internucleotide phosphodiester linkages are prepared from hydrogen phosphonate linkages preferably by oxidation with, e.g., aqueous iodine. A typical procedure involves treatment of the hydrogen phosphonate in 0.1 M iodine in Pyr/NMI/$H_2O$/THF (5:1:5:90) for about 2–3 minutes, followed by treatment with 0.1 M iodine in $Et_3$/$H_2O$/THF (5:5:90) for another approximately 2–3 minutes.

Phosphoromonothioate linkages are formed from the initially present hydrogen phosphonate linkages by treatment with sulfur as described in U.S. Pat. No. 5,256,775.

To form hydrogen phosphorodithioate linkages, sulfurization of the hydrogen phosphoromonothioate linkages is effected using conditions identical to those described for the preparation of the phosphoromonothioate moiety. (Note: the term "phosphorothioate" as used herein is intended to encompass both "phosphoromonothioate" and phosphorodithioate" linkages).

The modified oligonucleotides of the invention, are resistant to degradation under both physiological and tissue culture conditions, and in particular are resistant to degradation by exonucleases.

In order that the oligonucleotide be resistant to such enzymatic degradation, it is modified so that phosphodiester linkages initially present at the 3' terminus are replaced with a selected number of phosphoramidate linkages, that number being at least one and less than a number which would cause interference with binding to a target molecule. Such a modification may additionally or alternatively be made at the 5' terminus.

The oligonucleotides of the present invention may be also modified by the addition of groups to facilitate their entry into cells. Such groups include but are not limited to non-polypeptide polymers, polypeptides, lipophilic groups and the like. "Lipophilic" groups refer to moieties which are chemically compatible with the outer cell surface, i.e., so as to enable the oligonucleotide to attach to, merge with and cross the cell membrane. Examples of such lipophilic groups are fatty acids and fatty alcohols in addition to long chain hydrocarbyl groups. Such modified oligonucleotides and methods for making the oligonucleotides are disclosed in U.S. Pat. No. 5,256,775.

In one embodiment the oligonucleotides of by the present invention may be represented by the formula:

$[N_x\text{-GGC-}N_x]_z$ and modifications or derivatives thereof wherein;

N=nucleotide base or several bases selected from group consisting of A, T, G,C, U and modified bases x=is an integer from zero to 48;

z=is an integer from 1 to 33.

In one embodiment, x=0 and z=7.

In a particular embodiment the oligonucleotides of the present invention include but are not limited to:

| | |
|---|---|
| GTCCACCATGGCGCGGCCGGC | (SEQ ID No.: 1); |
| TCCGCGAACCCGGTGCGCCGG | (SEQ ID No.: 2); |
| TCCAGGCTGCTGCCCCATAAA | (SEQ ID No.: 3); |
| CCGACCACTTCCGAGTACTAG | (SEQ ID No.: 4); |
| CGCTGAAGTTTTGAACTCTGC | (SEQ ID No.: 5); |
| TGTACGTCCGGCTTACTAGTA | (SEQ ID No.: 6); |
| ODN1A 5' GGCGGCCGCGCTGCAA CCCGT 3' | (SEQ ID NO.: 7); |
| ODN1B 5' TGCCCAACGTCGCGCC GGCGG 3' | (SEQ ID NO.: 8); |
| ODN1C 5' GGCCGTGCAGCTCGCA CCGGC 3' | (SEQ ID NO.: 9); |
| ODN1D 5' TCCGCGAACCCGGTGC GCCGG 3' | (SEQ ID NO.: 10) | and modifications or derivatives thereof. Such modifications or derivatives include but are not limited to one or more modified groups such as all phosphodiester, all phosphorothioate, phosphorothioate capped linking groups one or more modified sugar residues and/or one or more modified bases and the like.

At least two methods may be employed to identify oligonucleotides containing at least one binding region that specifically binds a target of interest. The first method is an empiric method in which a set of oligonucleotides are synthesized, purified and screened for a desired activity as generally described in International Publication No. WO 92/14843. In the second method, a library of randomly synthesized oligonucleotides are screened for a desired activity as described by Bock (1992) *Nature* Vol. 355, 564–566. In general, the oligonucleotide containing at least one binding region for a target is allowed to bind the target. The oligonucleotide is separated from the target, isolated and amplified by the polymerase chain reaction (PCR) technique as known in the art.

In one embodiment, the oligonucleotide containing at least one binding region for a target is incubated with an immobilized target of interest with a mixture of member oligonucleotides under conditions such that the target of interest complexes or binds with some, but not all, members of the mixture to form oligonucleotide-target complexes. The oligonucleotide is eluted and isolated from the immobilized target using high salt concentrations. The eluted oligonucleotide fractions may be tested for activity. PCR technology is used to amplify the eluted oligonucleotides as disclosed in U.S. Pat. No. 4,683,195, U.S. Pat. No. 4,683, 202, Saiki, R K et al *Science* 239:487–491 (1988), and *Methods in Enzymology* 155:335–350 (1987). This constitutes a selection cycle. The cycle is repeated a number of times until an oligonucleotide is obtained which binds to the target with high affinity and possesses the desired biological activity, eg. inhibition of enzyme activity.

Accordingly, the oligonucleotides of the invention are useful in therapeutic, diagnostic and research contexts. In therapeutic applications, the oligonucleotides are utilized in a manner appropriate for aptameric therapy. Aptameric therapy as used herein includes targeting a target molecule such as a specific protein, peptide or derivative thereof through specific binding which results in preventing or inhibiting the biological function of the target molecule.

The oligonucleotides or mixtures of oligonucleotides of the present invention are useful in inhibiting the biological function of the target molecule both in vitro and in vivo. The oligonucleotides or mixtures of oligonucleotides of the present invention are particularly useful in inhibiting the enzymatic function of a target molecule both in vitro and in vivo. Of particular interest is the inhibition of the enzymatic activity of a protein kinase, especially protein tyrosine kinases such as p210BCR-ABL PTK and the like. As such, the oligonucleotide or mixtures of oligonucleotides of the present invention are effective in treating or preventing disease.

The oligonucleotides of the present invention comprises one or more nucleic acid sequences that bind to a protein or peptide for the purpose of inhibiting or preventing a disease. Such diseases include but are not limited to cancer, autoimmune diseases and diseases caused by pathogenic microorganisms.

Cancers which may be treated using the oligonucleotides or mixtures thereof of the present invention include but are not limited to melanoma, metastases, adenocarcinoma, thymoma, lymphoma, lung cancer, liver cancer, colon cancer, kidney cancer, non-Hodgkins lymphoma, Hodgkins lymphoma, leukemias, uterine cancer, breast cancer, prostate cancer, ovarian cancer, pancreatic cancer, brain cancer and the like. Of particular interest is chronic myelogenous leukemia, the etiology of which is dependent upon p210BCR-ABL PTK activity. Cancers particularly amenable to treatment using the oligodeoxynucleotides of the invention include cancers that are associated with overexpression of a gene product or expression of an altered gene product. The most commonly altered gene products in human solid tumors include but are not limited to $P210^{bcr-abl}$, ErbB/HER (a membrane-associated tyrosine kinase), Ras (a GTP-binding protein), and proteins that affect transcription, such as Rb, or p53 (Bishop, J. M. *Cell* 64, 235–248, 1991).

Overexpressed gene products which are associated with cancer include but are not limited to serine/threonine kinases (e.g. protein kinase C(PKC), CAWP-dependent protein kinase A [PKA], MYC, phosphorylase kinase, myosin light chain kinase) and tyrosine kinases (e.g. the epidermal growth factor receptor, Src, platelet-derived growth factor receptor), and the like.

The aforementioned cancers can be assessed or treated by methods described in the present application. In the case of cancer, the present invention is in no way limited to the oligonucleotides specifically disclosed herein. Other oligonucleotides may be identified and isolated by methods disclosed herein.

Autoimmune diseases that may be treated using the oligodeoxynucleotides of the invention include but are not limited to rheumatoid arthritis, systemic lupus erythematosus, thyroiditis, Goodpasture's syndrome and the like.

Diseases caused by pathogenic microorganisms may be prevented or treated using the oligonucleotides of the invention. In the case of pathogenic microorganism, the oligonucleotide contains at least one binding region capable of binding to a virulence factor of the microorganism. Such virulence factors are associated with causing disease. Such virulence factors include but are not limited to toxins, enzymes, cell wall components, capsules, pili and the like. Pathogenic microorganisms include but are not limited to viruses such as HIV (GP-120, p17, GP-160 antigens), influenza (NP, HA antigen), herpes simplex (HSVdD antigen), human papilloma virus, equine encephalitis virus, hepatitis (Hep B Surface Antigen), HCV and the like. Pathogenic protozoans include but are not limited to Trypanosomes, Plasmodia, Babesia, Schistosomia, Leishmania, and the like. Pathogenic yeast include Aspergillus, invasive Candida, Cryptosporidia, and the like. Pathogenic bacteria include but are not limited to *Mycobacterium tuberculosis, Staphylococcus aureus,* Group A Strep, and the like.

The present invention also encompasses methods of treatment or prevention of a disease caused by the disease causing agents disclosed here.

In the method of treatment, the administration of the oligonucleotides of the invention may be for either "prophylactic" or "therapeutic" purpose. When provided prophylactically, the oligonucleotides or mixtures thereof of the present invention is provided in advance of any symptom. The prophylactic administration of the oligonucleotide serves to prevent or ameliorate any subsequent infection or disease. When provided therapeutically, the oligonucleotides are provided at (or after) the onset of a symptom of infection or disease. Thus the present invention may be provided either prior to the anticipated exposure to a disease causing agent or after the initiation of the infection or disease.

The term "unit dose" as it pertains to the inoculum refers to physically discrete units suitable as unitary dosages for mammals, each unit containing a predetermined a quantity of oligonucleotide calculated to produce the desired inhibitory effect in association with the required diluent. The specifications for the novel unit dose of an inoculum of this invention are dictated by and are dependent upon the unique characteristics of the oligonucleotide and the particular effect to be achieved.

The inoculum is typically prepared as a solution in tolerable (acceptable) diluent such as saline, phosphate-buffered saline or other physiologically tolerable diluent and the like to form an aqueous pharmaceutical composition. In addition, the oligonucleotides may be formulated in solid form and redissolved or suspended prior to use. Lyophilized forms are also included.

The route of inoculation may be intravenous (I.V.), intramuscular (I.M.), subcutaneous (S.C.), intradermal (I.D.), intraperitoneal (I.P.), intrathecal (I.T.) and the like, which results in an inhibitory response against the disease causing agent.

Administration may also be by transmucosal or transdermal means, or the compounds may be administered orally. For transmucosal or transdermal administration, penetrants appropriate to the barrier to be permeated as used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the oligonucleotides are formulated into conventional oral administration forms such as capsules, tablets, and tonics.

For topical administration, the oligonucleotides of the invention are formulated into ointments, salves, gels or creams, as is generally known in the art.

In providing a mammal with the oligonucleotide of the present invention, preferably a human, the dosage of administered oligonucleotide will vary depending upon such factors as the mammal's age, weight, height, sex, general medical condition, previous medical history, disease progression, tumor burden and the like.

In general, it is desirable to provide the recipient with a dosage of oligonucleotide of at least about 0.005 mg/kg/hr, preferably at least about 0.05 mg/kg/hr, or in the range of from about 0.005 mg/kg/hr to about 0.5 mg/kg/hr in a mammal by preferably continuous I.V. infusion, although a lower or higher dose may be administered. The dose provides serum levels of oligonucleotide in the range of about 1 $\mu$M to about 100 $\mu$M. The dose is administered at least once. Subsequent doses may be administered as indicated.

The oligonucleotide or combination of oligonucleotides can be introduced into a mammal either prior to any evidence of cancers or to mediate regression of the disease in a mammal afflicted with a cancer. Examples of methods for administering the oligonucleotide into mammals include, but are not limited to, exposure of cells to the oligonucleotide ex vivo, or injection of the oligonucleotide into the affected tissue or organ or intravenous (I.V.), subcutaneous (S.C.), intradermal. (I.D.) or intramuscular (I.M.) administration and the like of the oligonucleotide. Alternatively the oligonucleotide or combination of oligonucleotide may be administered locally by direct injection into the cancerous lesion or topical application in a pharmaceutically acceptable carrier.

Cells to be treated may actively take up the oligonucleotides of the present invention. The oligonucleotides of the present invention may be incorporated into liposomes, in particular cationic liposomes, to enhance the cellular uptake and effectiveness of the oligonucleotides. The oligonucleotides may also be modified by the addition of groups to facilitate their entry into cells. Such groups include polypeptide polymers, polypeptides, lipophilic groups and the like. Alternatively, the oligonucleotides of the present invention be introduced into the cells to be treated by electroporation, and other methods that enhance the cellular uptake of the oligonucleotide.

After treatment the efficacy of the oligonucleotide can be assessed by determination of alterations in activity of the target molecule or determination of effects upon downstream molecules, tumor regression, or a reduction in the pathology or symptoms associated with the disease. One skilled in the art would know the conventional methods to assess the aforementioned parameters. If the mammal to be treated is already afflicted with the disease the oligonucleotide can be administered in conjunction with other therapeutic treatments.

In addition, to use in therapy, the oligonucleotides of the invention may be used as diagnostic reagents to detect the presence or absence of the target molecule such as a peptide, protein or derivatives thereof to which the oligonucleotide specifically binds. Such diagnostic tests are conducted by binding of the oligonucleotide of the invention to its specific target molecule such as a peptide, protein, or derivative thereof which is then detected by conventional means. For example, the oligonucleotide may be labeled using radioactive, fluorescent, or chromogenic labels and the presence of the label bound to a solid support detected.

The present invention also encompasses combination therapy. By comibination therapy is meant that the ODN or mixture thereof is administered to the patient in combination with other exogenous immunomodulators or immunostimulatory molecules, chemotherapeutic drugs, antibiotics, antifungal drugs, antiviral drugs and the like alone or in combination thereof. Examples of other exogenously added agents include exogenous IL-2, IL-6, interferon, tumor necrosis factor, cyclophosphamide, and cis platinum, gancyclovir, amphotericin B and the like.

Cells that are amenable to treatment by the oligonucleotides of the present invention include but are not limited to cells containing an oncogene where overexpression of the oncogenic protein results in excessive cell growth and neoplasms, leukemia cells, cells overexpressing a signal transduction regulatory protein, cells overexpressing protein kinase, cells overexpressing protein tyrosine kinase, cells overexpressing $p_{210}^{bcr-abl}$ kinase, cells overexpressing abl kinase, cells infected with a disease causing microorganism and the like.

The oligonucleotides and derivatives thereof are useful for the induction of a disease state. In the cases where the induction of a disease is dependent upon decreased protein-tyrosine kinase (PTK) activity, it is possible to induce a disease-like state in an animal model, by inhibiting PTK activity with the aptameric oligonucleotides and derivatives thereof of the present invention. Such animal models are useful in studies of the molecular mechanism of the disease and pathology and in development and screening of therapeutics to reverse or control the disease-like state.

The present invention includes methods for screening for effective oligonucleotides that bind and inhibit a protein kinase in a cancer cell. Oligonucleotides and analogs thereof may be synthesized as described in Example 1. The synthesized oligonucleotides are screened using the combination of the cellular phosphotyrosine content and ability to inhibit cell growth of the cancer cell in soft agar as described herein. Cells useful in the screening assay include but are not limited to K 562 and the like.

The oligonucleotides of the invention are useful in methods to detect the presence or absence of a target molecule in vivo or in vitro. To detect the presence or absence of a target molecule, a biological sample suspected of containing the target molecule is contacted with an oligonucleotide having at least one binding region capable of binding specifically to the target under conditions that a complex forms between the target molecule and the oligonucleotide. The presence or absence of the complex is detected. The biological sample may be a tissue, cell or fluid sample. The method may be qualitative or quantitative in detecting not only the presence or absence of the target molecule, but also the amount of the target molecule calculated from a known set of standards. The presence or absence of the complex may be detected by conventional methods known in the art. Methods used to detect antigens or antibodies may be modified to detect target molecules using a oligodeoxynucleotide specific for the target molecule as the capture and/or detecting agent. Such methods are useful as a diagnostic screen for a disease caused by/or is indirectly the result of the target molecule in a patient.

The oligonucleotides of the invention are useful in the isolation and purification of target molecules to which the oligonucleotides specifically bind. For this application, typically, the oligonucleotide containing at least one binding region capable of binding specifically to a target molecule is conjugated to a solid support and used as an affinity ligand in chromatographic separation of the target molecule. The affinity ligand can also be used to recover previously unknown substances from sources due to similarities in structure and/or conformation between the target molecule and the unknown substance. The purity of an isolated protein, peptide or derivative is greater than 75%, preferably at least 90% and more preferably at least 95% or greater purity based on total protein.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments.

All references and patents referred to are incorporated herein by reference.

EXAMPLE 1

Materials and Methods

Cell Cultures

K562, NIH 3T3, and A431 cells were purchased from the American Type Culture Collection (Rockville, Md.). PC3M prostate cancer cells were a generous gift from J. Trepel (National Institutes of Health, Bethesda, Md.). K562 and PC3M cells were cultured in RPMI 1640 with 10% heat-inactivated fetal bovine serum (FBS; GIBCO BRL, Grand Island, N.Y.) while NIH 3T3 and A431 cells were cultured in Dulbecco's modified Eagle's medium (Biofluids, Rockville, Md.) with 10% heat inactivated FBS. Cells were maintained at 37° C., 6% carbon dioxide with biweekly media changes. For soft agar cloning, cells were suspended in 0.3% low melting temperature agarose (SeaPlaque FMC BioProducts, Rockland, Me.) in RPMI 1640 with 10% total calf serum and maintained as above.

Source of PTKs

The $p_{210}^{bcr-abl}$ kinase, src kinase and cdc-2 kinase were immunoprecipitated from K562 cells. The $p145^{abl}$ kinase was immunoprecipitated from PC3M cells, PDGF receptor kinase from 3T3 cells, and EGF receptor kinase from A431 cells. MAP kinase was utilized as a pure protein and lck kinase was immunoprecipitated from peripheral blood lymphocytes of a normal volunteer.

Oligodeoxynucleotide synthesis

Oligonucleotides (ODNs) were synthesized by cyanoethyl phosphoroamidite chemistry on an Applied Biosystems model 380B DNA synthesizer according to the manufacturers instructions. Sulfurizing reagent (Glen Research, Sterling, Va.) was used according to the manufacturer's instructions. Following cleavage from the solid support, samples were ethanol precipitated, washed in 70% ethanol, and resuspended in sterile water. Aliquots were resolved on a denaturing polyacrylamide gel to check for homogeneity. The sequence of ODN1 or BCR-AS is 5'-GTCCACCATGGCGCGGCCGGC-3' (SEQ ID NO.: 1) and unless otherwise specified is phosphorothioate capped in all experiments; it is complementary to nucleotides −12 to +9 of the $p210^{bcr-abl}$ mRNA (+1 is the translation start site); BCR-SCR: 5'TCCGCGAACCCGGTGCGCCGG-3 (SEQ ID NO.: 2); the scrambled version of BCR-AS; ABL-1bAS: 5'-TCCAGGCTGCTGCCCCATAAA-3' (SEQ ID NO.: 3); complementary to nucleotides −3 to +18 of the abl 1b mRNA; ABL-1bSCR: 5' CCGACCACTTCCGAGTACTAG-3' (SEQ ID NO.: 4) the scrambled version of ABL-1bAS; B/A-As: 5'-CGCTGAAGTTTTGAACTCTGC-3' (SEQ ID NO.: 5); spans the bcr-abl fusion region and is complementary to 11 bcr and 10 abl nucleotides of the mature fusion transcript. B/A-SCR: 5'-TGTACGTCCGGCTTACTAGTA-3' (SEQ ID NO.: 6); the scrambled version of B/A-SCR. T-21; a 21mer composed solely of thymidylic acid residues. All phosphorothioate capped ODNs contain two interbase phosphorothioate linkages at both 5' and 3' ends with phosphodiester linkages in between, except the tetramer GGCG which only contains one phosphorothioate linkage at each end. ODNs modified with 2'-methoxy ribose were purchased from Integrated DNA Technologies Inc. (Colalville, Iowa).

Preparation of cell lysates

Cells were washed in phosphate buffered saline (PBS) and $0.5–5\times10^6$ cells were solubilized in 1 ml of the specified cell lysis buffers. Unless otherwise stated, all cell lysis buffers contained the following protease inhibitors: 20 µg/ml leupeptin, 1 µg/ml aprotinin, and 1 mM phenylmethylsulfonylfluroide. For $p210^{bcr-abl}$ and $p145^{bcr-abl}$ immunoprecipitation, cells were lysed with ABL lysis buffer (25 mM imidazole, pH 7.2, 0.5% NP40, 50 mM NaCl, 1 mM $Na_3VO_4$) and lysates were clarified at 14,000 g. 4° C. for 30 minutes. Cell lysis for all other proteins was performed according to the references describing the various immunoprecipitation kinase assays.

Immunoprecipitation kinase assays

Immunoprecipitation kinase assays of $p_{210}^{bcr-abl}$ $p145^{abl}$ were performed as described, with modifications (15). Briefly, for $p210^{bcr-abl}$, 1 µg of anti-bcr antibody (clone 7C6, Oncogene Science, Uniondale, N.Y.) was added to lysates prepared from $0.5–1\times10^6$ K562 cells. For $p145^{abl}$, 1 µg of anti-c-abl antibody (clone 24-21), which binds to the C-terminal domain of $p145^{abl}$, was added to lysates prepared from $5\times10^6$ PC3M cells. After incubating 1 hour at 4° C., complexes were precipitated by incubating with protein A-Sepharose coated with rabbit anti-mouse immunoglobulin (Cappel Research Products, Durham, N.C.) for 30 minutes. The complexes were then washed as follows: ABL lysis buffer×2, PBS×1, and ABL assay buffer×1 (24 mM imidazole, pH 7.2, 1 mg/ml bovine serum albumin, and 10 mM MnCl). For $p145^{abl}$ assays ABL assay buffer contained 20 mM MnCl. To access the activity of $p210^{bcr-abl}$ on substrate phosphorylation, acid inactivated enolase (Sigma Chemical Co., St. Louis, Mo.) was added as described (15).

Epidermal growth factor receptor (EGFR) was immunoprecipitated with 10 ,g anti-EGFR antibody (clone LA1) and human recombinant epidermal growth factor (both from Upstate Biotechnology Inc., Lake Placid, N.Y.). The assay was performed as described (17) but without removing the EGFR from the protein A-antibody solid support. Instead, epidermal growth factor, at a final concentration of 100 nM, was added to the kinase reaction mixture. Platelet derived growth factor receptor (DGFR) was immunoprecipitated with anti-human type A/type B PDGFR antibody (Upstate Biotechnology Inc.) and immune complex kinase assays performed as referenced (18) except that protein A-Sepharose coated with rabbit anti-mouse immunoglobulin was used instead of formalin-fixed *Staphylococcus aureus* to bind PDGFR-antibody conjugates. C-src was immunoprecipitated with anti-v-src antibody (Ab-1; Oncogene Science) and assayed as previously described (19) with the addition of enolase as exogenous substrate. Lck was immunoprecipitated using anti-lck antibody (Upstate Biotechnology Inc.) and assayed as described (19). Cdc-2 Idnase (20) was isolated with affinity purified rabbit antibody (a generous gift of Jean Wang, University of California, San Diego, Calif.) and assayed with casein that was dephosphorylated as described by Mayer (21). MAP kinase was assayed as previously described (22) using purified enzyme (Upstate Biotechnology Inc.).

ODNs were added to kinase reaction buffers not more than 5 minutes prior to the addition of ATP. Reactions were initiated by the addition of [$\gamma$-$^{32}$P] ATP (3000 Ci/mmole; Amersham Corp., Arlington Heights, Ill.) and quenched by the addition of 5× gel loading buffer and heating to 95° C. Kinase reactions were run for 1–10 minutes at room temperature, except for EGFR, p145$^{abl}$, and MAP kinase, which were run at 30° C. The products were then electrophoresed on SDS-polyacrylamide gels: 7% for p210$^{bcr-abl}$, EGFR, and PDGFR, 8% for p145$^{abl}$, 10% for src, lck, and cdc-2 kinase, and 12% for MAP kinase. Gels were dried and reaction products were visualized by direct autoradiography at −70° C. with Kodak X-OMAT AR film. To determine the inhibitory concentration 50, i.e., the concentration required to inhibit enzyme activity by 50% (IC$_{50}$) and K$_i$ values, gel slices containing the band of interest were excised and analyzed by Cerenkov counting.

Western Blotting

One hundred micrograms of protein from cell lysates were separated on a 7% SDS polyacrylamide gel. Transfer was performed overnight at 50 volts, 4° C., in a 0.2 M glycine, 25 mM Tris, pH 8.3, 0.15% SDS, 20% methanol buffer, onto 0.45 μM nitrocellulose (Schleicher and Schuell Inc.). For cellular phosphotyrosine blots, Western probing was performed as described previously, with modifications (SARTOR, et al, 1991). Briefly, membranes were blocked for 2 hours with 5% albumin in TTBS (20 mM Tris HCL, pH 7.6; 0.05% Tween 20; 0.9% sodium chloride), probed for 1 hour with antiphosphotyrosine antibody (Upstate Biotechnology Inc., Lake Placid, N.Y.) diluted 1:500 in TTBS, followed by rabbit anti-mouse antibody (Cappel Research Products) and then [$^{125}$I] protein A Sepharose (Amersham Corp., Arlington Heights, Ill.). Membranes were exposed to Kodak X-OMAT AR film overnight at −70° C. with intensifying screens.

For p210$^{bcr-abl}$ Western analysis, probing was carried out with the ECL Western blotting kit (Amersham) according to manufacturer's instructions. Briefly, membranes were blocked in 5% non-fat dry milk in TTBS for 1 hour, incubated with anti-p210$^{bcr-abl}$ antibody (clone 8E9, Pharmingen, San Diego, Calif.) diluted 1:500 in TTBS for 1 hour, with sheep anti-mouse horseradish peroxidase-linked antibody (diluted 1:1000) for 1 hour, and lastly incubated in a luminol based detection solution for 1 minute. Membranes were exposed to Kodak X-OMAT AR film for various time periods.

Electroporation

Electroporation was performed as described (40). Briefly, 1–5×10$^6$ cells in 1 ml of RPMI 1640 with 10% fetal calf serum were placed into 0.4 cm gap electroporation chambers and electroporated with a Cell-Porator Electroporation System 1 (all from GIBCO BRL, Grand Island, N.Y.) at 800 microfarrads, 300 volts, at room temperature. Cells were then incubated at 37° C. for 1 hour before manipulation.

EXAMPLE 2

Inhibition of p210$^{bcr-abl}$ Kinase Activity By ODN1

Figure 1B:
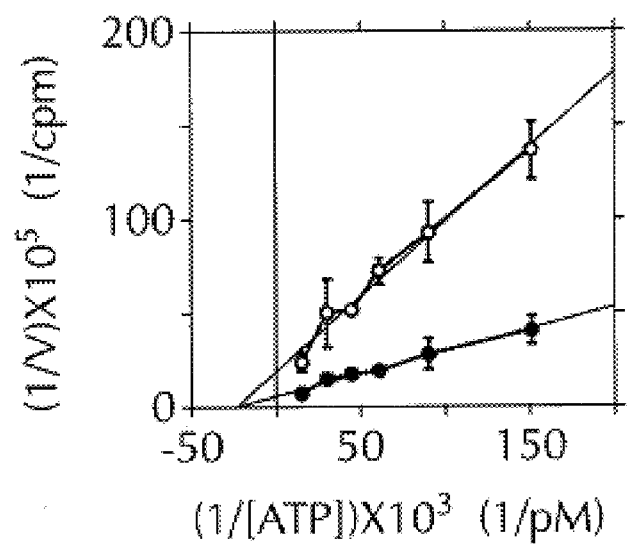
FIG. 1B Inhibition of $p210^{bcr-abl}$ kinase activity by ODN1. Double-reciprocal plot of $p210^{bcr-abl}$ kinase activity, as determined by Cerenkov counting of excised polyacrylamide gel slices, in the absence (closed circles) and presence (open circles) of 1 µM ODN1. The data represent the mean ± SD of a single experiment run in duplicate. Similar results were obtained in a separate experiment also run in duplicate.

The in vitro inhibition of p210$^{bcr-abl}$ kinase activity by ODN1 can be seen in FIG. 1A. Kinase activity is markedly inhibited by pre-incubation of the immunoprecipitated enzyme with 1 μM ODN1. To determine the nature of the enzymatic inhibition and to quantitate the potency of inhibition, enzyme activity was determined at various [$\gamma$-$^{32}$P]ATP concentrations in the presence or absence of 1 μM ODN1. FIG. 1B depicts the double-reciprocal plot of enzyme activity as determined by Cerenkov counting of excised SDS gel slices. ODN1 apparently inhibits the p$_{210}{}^{bcr-abl}$ kinase in a purely noncompetitive manner with respect to ATP, with a K$_i$ of 0.52±0.12 μM.

The p210$^{bcr-abl}$ protein is the product of a chromosomal translocation leading to the formation of a fusion transcript (23, 24) In the fusion protein there is replacement of the normal abl N-terminal sequences with the N-terminal sequences of the bcr protein. This leads to a relative lack of regulation with a subsequent increase in PTK activity (25). There is evidence to suggest that both the loss of native abl sequences and interactions with N-terminal bcr sequences have effects upon kinase activity (26, 27). To determine if the bcr moiety is important in mediating the inhibitory effects of ODN1, its ability to inhibit p145$^{abl}$ kinase activity was tested (see Table 1). The results demonstrate that both p145$^{abl}$ and p210$^{bcr-abl}$ are equally sensitive to ODN1. To determine whether ODN1 can also inhibit the ability of either p145$^{abl}$ or p210$^{bcr-abl}$ to phosphorylate substrates, enolase was added to the kinase reactions; at ODN1 concentrations of up to 50 μM there was no significant inhibition of enolase phosphorylation (data not shown).

TABLE 1

IC$_{50}$ Values of ODN1 Against Various Protein Kinases*

| Protein kinase | IC$_{50}$ (μM) |
| --- | --- |
| Tyrosine kinases | |
| BCR-ABL | 0.52 ± 0.12 |
| ABL | 0.62 ± 0.24 |
| SRC | >100 |
| LCK | >50 |
| EGFR | >100 |
| PDGFR | 4.4 ± 2.3 |
| Serine/threonine kinases: | |
| cdc -2 kinase | >50 |
| MAP kinase | >100 |

*Enzyme activity was determined by Cerenkov counting of excised gel slices. Values are the mean ± SD of two separate experiments, each composed of dual determinations.

EXAMPLE 3

Inhibitory Properties of Oligodeoxynucleotides As A Function of Sequence

To determine if the inhibitory properties of ODN1 are a function of sequence, four phosphorothioate capped scrambled sequences (based on OND1) were synthesized and their effect upon the inhibition of p210$^{bcr-abl}$ kinase activity at 1 μM was compared to that of ODN1 (Table 2). By comparing the percent inhibition seen with each ODN with its sequence, it appears that the presence of closely spaced GGC repeats contributes significantly to the ability of a particular ODN to inhibit p210$^{bcr-abl}$ activity.

TABLE 2

Inhibition of p210$^{bcr-abl}$ Kinase Activity In Vitro By
Phosphorothioate Capped ODNs of Various Sequence

| | Sequence | Percent Remaining Activity* | |
|---|---|---|---|
| ODN1 | 5' GTCCACCATGGCGCGGCCGGC 3' | 36 ± 1.2 | (SEQ ID NO.: 1) |
| ODN1A | 5' GGCGGCCGCGCTGCAACCCGT 3' | 42 ± 6.9 | (SEQ ID NO.: 7) |
| ODN1B | 5' TGCCCAACGTCGCGCCGGCGG 3' | 59 ± 6.4 | (SEQ ID NO.: 8) |
| ODN1C | 5' GGCCGTGCAGCTCGCACCGGC 3' | 74 ± 15 | (SEQ ID NO.: 9) |
| ODNID | 5' TCCGCGAACCCGGTGCGCCGG 3' | 79 ± 79 | (SEQ ID NO.: 10) |

*Percent activity remaining refers to percent of activity relative to control as determined by Cerenkov counting of excised gel slices as described in Experimental procedures. All ODNs were added to a final concentration of 1 μM. ODNs 1A—1D are scrambled versions of ODN1. Values are expressed as the mean of ± SE of three separate experiments.

Figure 2A:
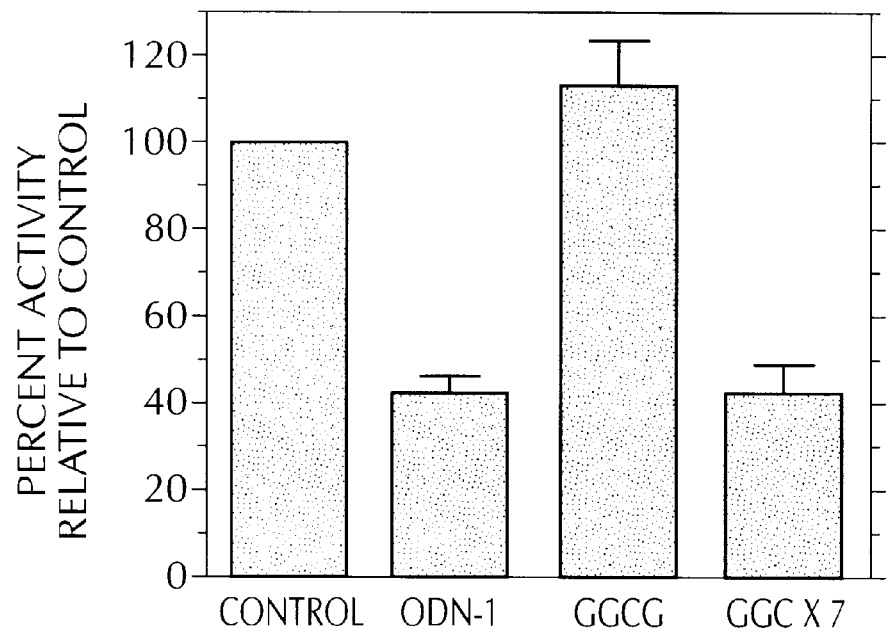
FIG. 2A. Inhibition of $p210^{bcr-abl}$ kinase activity in vitro by ODNs of altered sequence. Activity was measured in the absence (control) or presence of the following phosphorothioate capped ODN species: ODN1, GGCG tetramer, and a 21mer consisting of seven tandem GGC repeats (GGC X7). The activity of $p210^{bcr-abl}$ kinases was determined by excision of gel slices as explained in Experimental procedures; all ODNs were present at 1 μM. Values are the mean ± SE of three separate experiments.

To test this hypothesis, the ability of ODNs consisting only of GGC repeats to inhibit kinase activity was determined (FIG. 2A). With a 21-mer sequence (the same length as ODN1) consisting of seven tandem GGC repeats i.e., 5' GGCGGCGGCGGCGGCGGCGGC 3', (SEQ ID NO.: 11), inhibitory activity equivalent to ODN1 is seen. However, the tetramer GGCG had no inhibitory activity, again suggesting the requirement for GGC repeats.

Figure 2B:
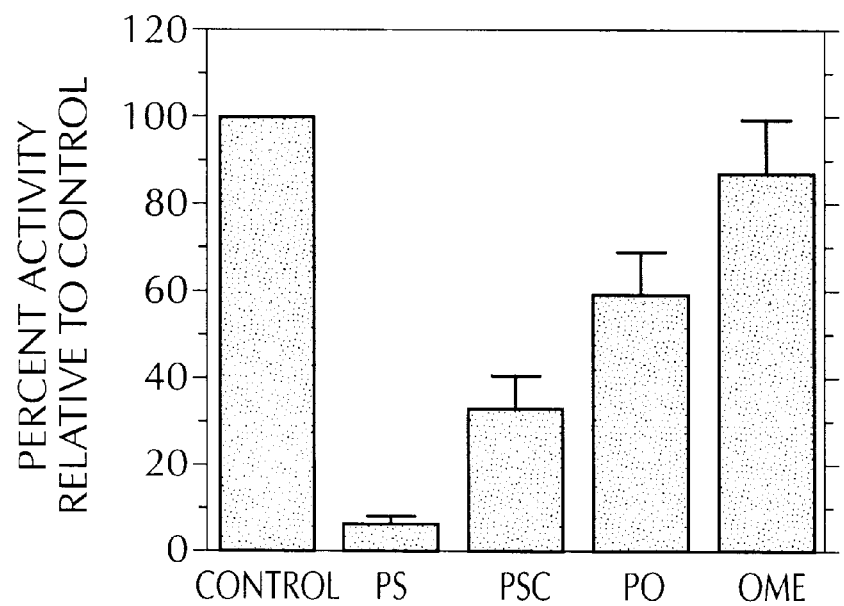
FIG. 2B. Inhibition of $p210^{bcr-abl}$ kinase activity in vitro by ODNs of altered backbone structure. Activity was measured in the absence (control) or presence of ODN1 with various backbone modifications: PO, all phosphodiester; PS, all phosphorothioate; PSC, phosphorothioate capped; OME, all phosphodiester 2'-methoxy ribose modified. The activity of $p210^{bcr-abl}$ kinases was determined by excision of gel slices as explained in Experimental procedures; all ODNs were present at 1 μM. Values are the mean ± SE of three separate experiments.

To determine the significance of backbone structure to this phenomenon, ODN1 was synthesized with four different backbone structures as follows: all phosphodiester, all phosphorothioate, phosphorothioate capped, and all phosphodiester with 2'-methoxy modified sugars. The ability of these sequences to inhibit p210$^{bcr-abl}$ kinase activity at 1 μM was then determined (FIG. 2B). It is evident that backbone modification can significantly affect the ability of ODN1 to inhibit the kinase. ODN1 with an all phosphorothioate backbone was the most potent inhibitor, while the version of ODN1 containing 2'-methoxy modified sugars was the least effective. The phosphorothioate capped and the all phosphodiester species have intermediate potencies. Prior nuclease digestion of the phosphodiester congener of ODN1 completely abrogated its inhibitory potential (data not shown).

EXAMPLE 4

Specificity of ODN1 For Various Protein Tyrosine Kinases

Figure 3A:
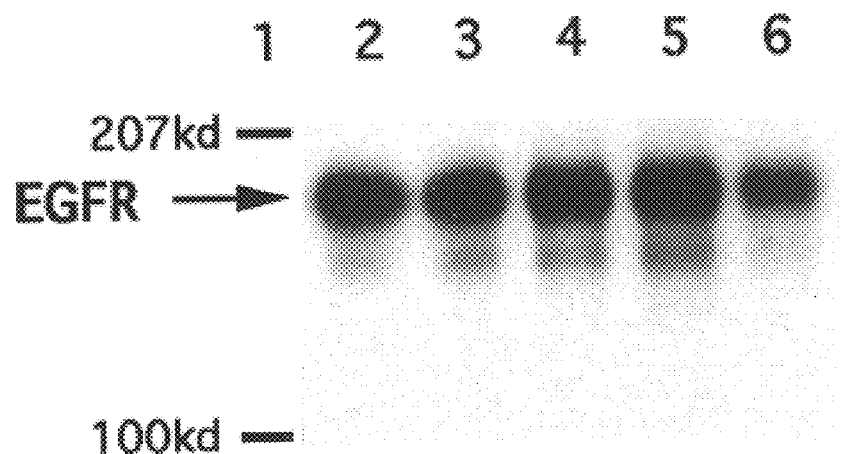
FIG. 3A. Inhibition of epidermal growth factor receptor (EGFR) autophosphorylation in vitro by ODN1. Immunoprecipitation kinase assays were performed as described in Example 1, in the absence of (Lane 2), or with increasing amounts of ODN1 present as follows: Lane 3, 0.1 μM; Lane 4, 1 μM; Lane 5, 10 μM; Lane 6, 100 μM; Lane 1, molecular weight standards.
Figure 3B:
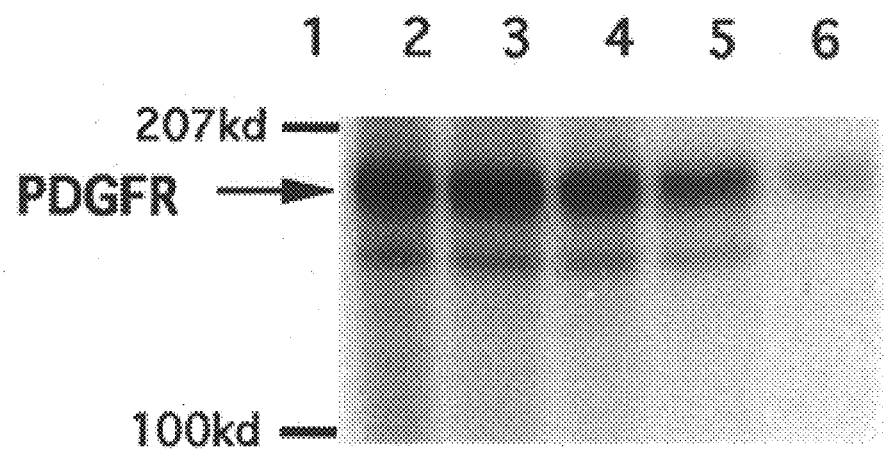
FIG. 3B. Inhibition of platelet derived growth factor receptor (PDGFR) autophosphorylation in vitro by ODN1. Immunoprecipitation kinase assays were performed as described in Experimental procedures, in the absence of (lane 2), or with increasing amounts of ODN1 present as follows: lane 3, 0.1 μM; lane 4, 1 μM; lane 5, 10 μM; lane 6, 100 μM; lane 1, molecular weight standards.

The specificity of ODN1's inhibitory activity was evaluated by testing its ability to inhibit several other PTKs and serine/threonine kinases. Table 1 lists the IC$_{50}$ values. The data demonstrate that all kinases are not equally sensitive to this ODN. Only one other PTK examined, the PDGF receptor, demonstrated sensitivity, although this kinase was almost a log less sensitive than either p145$^{abl}$ or p210$^{bcr-abl}$. Other PTKs, including src, lck and the EGF receptor were not significantly inhibited at ODN1 concentrations greater than 2 logs above the K$_i$ for p210$^{bcr-abl}$. Interestingly, while PDGF and EGF receptors are PTKs with extensive amino acid sequence homology (28), they display a marked difference in sensitivity to ODN1 (FIG. 3).

EXAMPLE 5

Inhibitory Activity of ODN1 On Cellular Functions

Figure 4:
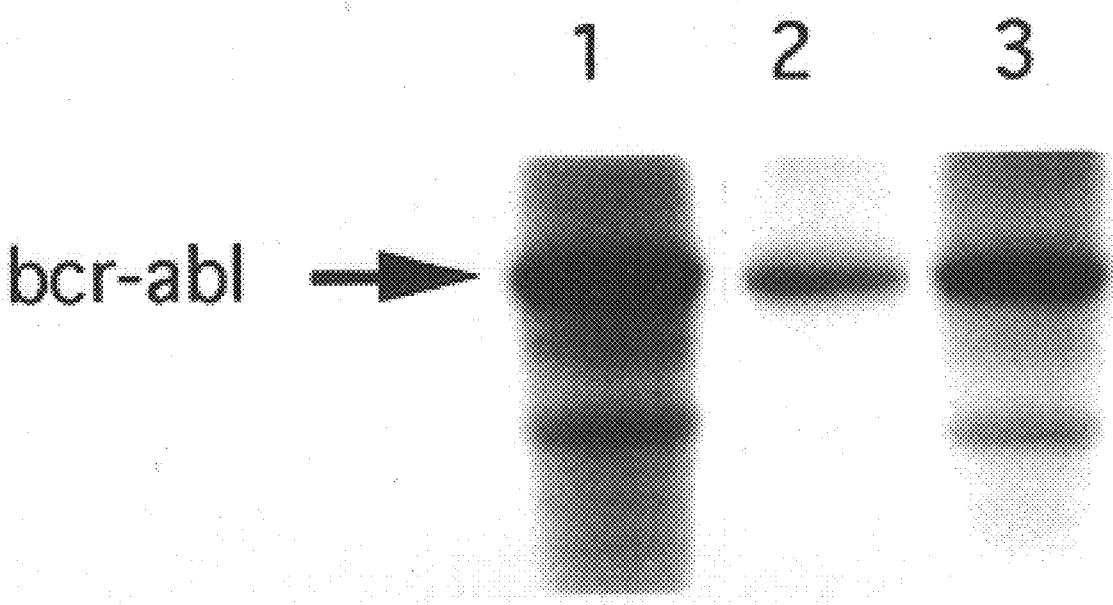
FIG. 4. Immunoprecipitation kinase assay of $p210^{bcr-abl}$ from K562 cells treated with ODNs for 3 days. K562 cells were seeded at $0.5 \times 10^6$/ml and allowed to grow for 3 days in the presence of either 50 μM ODN1 (lane 2) or ODN 1D (lane 3); lane 1, no ODN. The kinase activity of $p210^{bcr-abl}$ oll isolated from an equal number of cells was then assessed as described in Example 1.

The effects of ODN1 on a cellular system were assessed. K562 cells in liquid culture were incubated in the presence of either 50 μM ODN1, or with a scrambled version of ODN1 that does not inhibit kinase activity (ODN1D from Table 2). After 3 days, cells were washed and p$_{210}$$^{bcr-abl}$ kinase activity was measured. It can be seen in FIG. 4 that in ODN1 treated cells the activity of p210$^{bcr-abl}$ is significantly decreased relative to the scrambled and untreated control cells. Neither cellular p210$^{bcr-abl}$ protein content nor cell growth was affected by ODN treatment (data not shown).

EXAMPLE 6

Intracellular effects of oligodeoxynucleotides upon kinase activity and protein level of p210$^{bcr-abl}$, and upon total cellular phosphotyrosine content.

In K562 cells p210$^{bcr-abl}$ is a major kinase responsible for protein tyrosine phosphorylation (38, 39). Changes in enzyme activity are therefore reflected by changes in cellular phosphotyrosine content. Since electroporation has been previously demonstrated to be a simple and reproducible means of generating high intracellular ODN levels, this technique was used to rapidly load cells with several ODNs (40). One hour following electroporation of BCR-AS into K562 cells, total cellular protein phosphotyrosine content was examined by Western blotting and was found to have dropped significantly (FIG. 5, lane 3) compared to cells electroporated in the absence of ODN (FIG. 5, lane 2).

With several other ODNs tested, however, there was a poor correlation between the ability to decrease total cellular phosphotyrosine levels and the ability to inhibit p210 kinase activity. BCR-SCR and B/A-SCR (FIG. 5, lanes 4 and 8, respectively) effectively lowered protein phosphotyrosine content in a cellular system. However, the former ODN did not inhibit kinase activity, while the later ODN did (FIG. 6A, lanes 2 and 4). ABL-1bAS, ABL-1bSCR and B/A-AS ODNs had less marked effects upon total cellular phosphotyrosine content (FIG. 5, lanes 5, 6 and 7, respectively). While B/A-AS inhibited kinase activity (see FIG. 6A, lane 3), the ABL-1b related ODNs had minimal effects upon kinase activity (data not shown).

Figure 5:
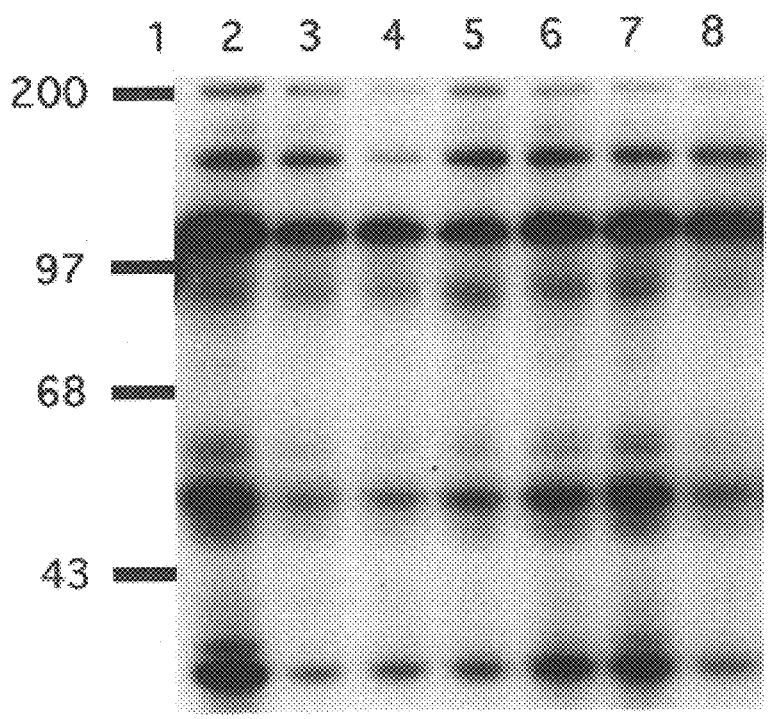
FIG. 5. Phosphotyrosine content of K562 cells after electroporation in the presence of various ODNS. K562 cells were electroporated in the presence of various ODNs at 100 μM. One hour later cells were lysed and western analysis for phosphotyrosine was performed on equal amounts of protein. Lane 1, MW stds; lane 2, control=no OLGN; lane 3, BCR-AS=GTCCACCATGGCGCGGCCGGC (SEQ ID No.: 1); lane 4, BCR-SCR=TCCGCGAACCCGGTGCGCCGG (SEQ ID No.: 2); lane 5, ABL-1bAS=TCCAGGCTGCTGCCCCATAAA (SEQ ID No.: 3); lane 6, ABL-1bSCR=CCGACCACTTCCGAGTACTAG (SEQ ID No.: 4); lane 7, B/A-AS=CGCTGAAGTTTTGAACTCTGC (SEQ ID No.: 5); lane 8, B/A-SCR=TGTACGTCCGGCTTACTAGTA (SEQ ID No.: 6). Similar results were obtained in a second experiment.
Figure 6A:
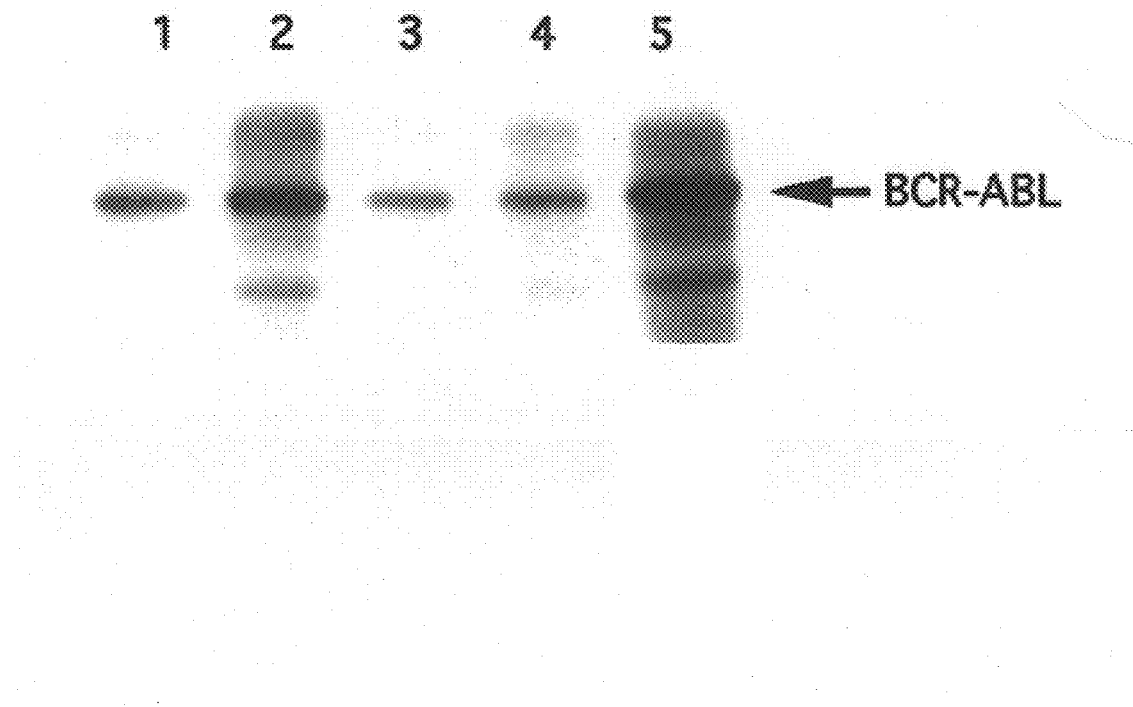
FIG. 6A. Immunoprecipitation-kinase assay for $p210^{bcr-abl}$ on ODN treated K562 cells. Autoradiograph of $p210^{bcr-abl}$ immunoprecipitation-kinase assay. K562 cells were incubated for 3 days in the presence of 50 μM ODN, washed with phosphate buffered saline, and a $p210^{bcr-abl}$ immunoprecipitation-kinase assay was performed. BCR-AS (lane 1), BCR-SCR (lane 2), B/A-AS (lane 3), B/A-SCR (lane 4), or no ODN control (lane 5). Results are representative of several experiments.
Figure 6B:
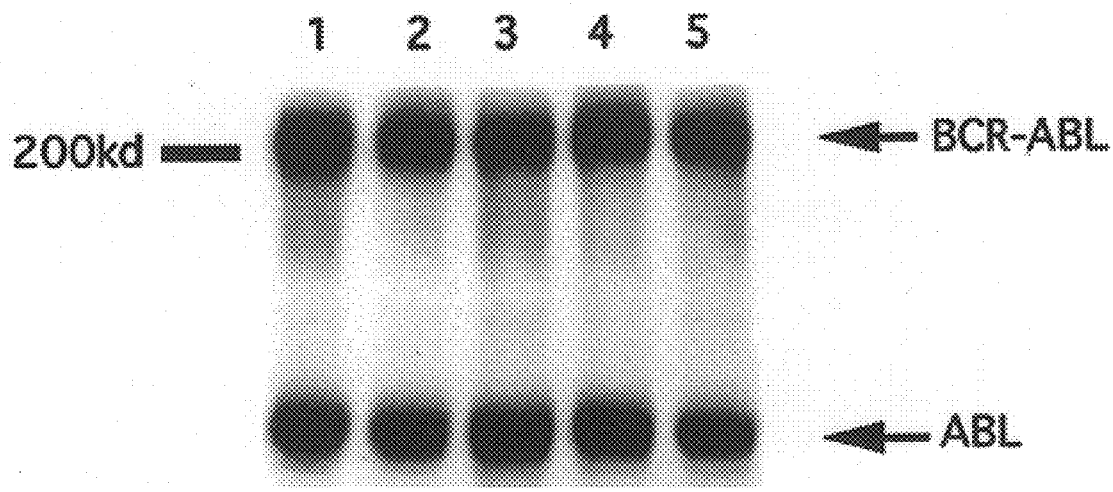
FIG. 6B. Western analysis of $p210^{bcr-abl}$ after electroporation of K562 cells in the presence of various ODNs. K562 cells were electroporated in the presence of 100 μM ODN and one hour later cells were washed with phosphate buffered saline, lysed, and equal amounts of protein were separated on a 7% SDS polyacrylamide gel. After transfer, Western analysis with the ABL-directed antibody, clone 8E9, was performed. BCR-AS (lane 1), BCR-SCR (lane 2), B/A-AS (lane 3), B/A-SCR (lane 4), or no ODN control (lane 5). Results are representative of several experiments.

Although the BCR-AS ODN is complementary to a portion of bcr-abl mRNA, neither the decrease in cellular protein phosphotyrosine content observed in FIG. 5, nor the reduction of p210$^{bcr-abl}$ kinase activity observed in FIG. 6A, was due to antisense-mediated reduction in p210$^{bcr-abl}$ protein content. One hour after electroporation in the presence of several different ODNs at 100 μM including BCR-AS, there was no decrement in $p_{210}^{bcr-abl}$ protein level (FIG. 6B). There was also no decrease in $p210^{bcr-abl}$ levels following the ABL-1b related ODNs nor was any decrease detected if cells were exposed to 100 µM of any of these ODNs for up to 10 days (data not shown).

Figure 7A:
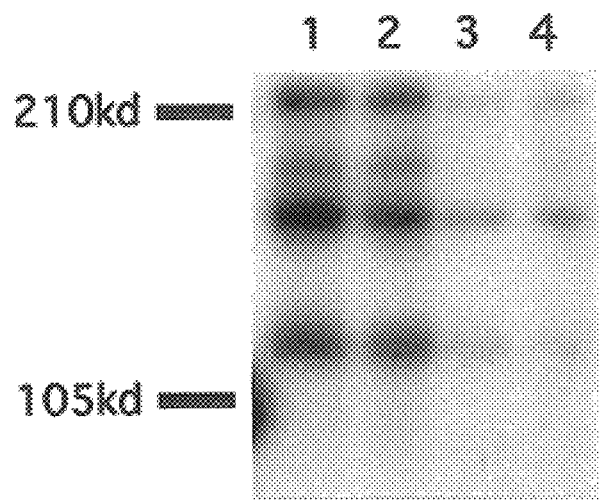
FIG. 7A. Effect of oligodeoxynucleotide backbone modification upon cellular phosphotyrosine levels. K562 cells were electroporated in the presence of 100 μM BCR-AS with the following backbone structure: all phosphorothioate (lane 2), all-phosphodiester (lane 3), phosphorothioate capped (lane 4), or no ODN control (lane 1). One hour later equal amounts of protein were run on a 7% SDS polyacrylamide gel, transferred to nitrocellulose, and probed for phosphotyrosine. Data are representative of three experiments.
Figure 7B:
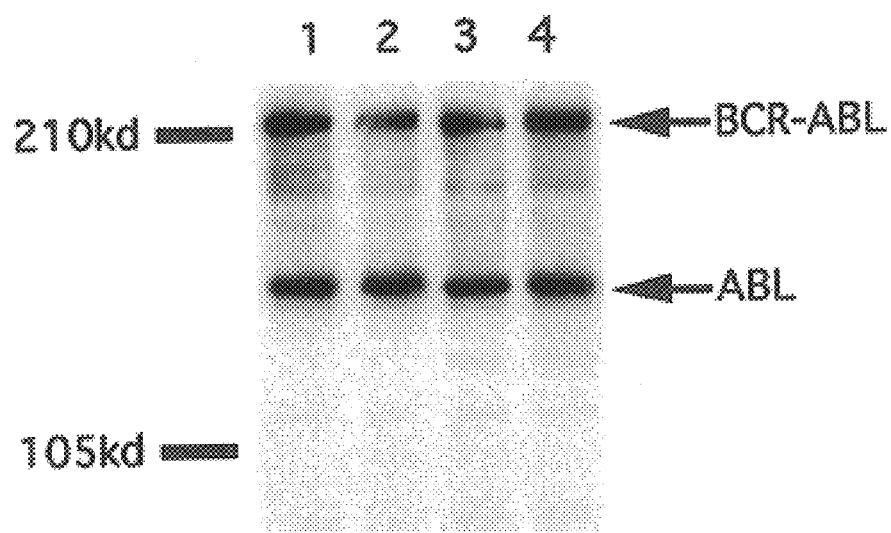
FIG. 7B. Effect of oligodeoxynucleotide backbone modification upon cellular phosphotyrosine levels. K562 cells were electroporated in the presence of 100 μM BCR-AS with the following backbone structure: all phosphorothioate (lane 2), all-phosphodiester (lane 3), phosphorothioate capped (lane 4), or no ODN control (lane 1). One hour later equal amounts of protein were run on a 7% SDS polyacrylamide gel, transferred to nitrocellulose, and probed for $p185^{abl}$ and $p210^{bcr-abl}$ with the ABL directed antibody, clone 8E9. Data are representative of three experiments.

All of the above studies were carried out using phosphorothioate capped ODNS. Different backbone modifications impart different properties to a particular ODN. For example, all-phosphodiester ODNs are susceptible to rapid exo- and endonuclease digestion and therefore have short half lives, while all-phosphorothioate ODNs have a propensity to bind to proteins nonspecifically (34). It was shown above in Example 3 at the all-phosphorothioate species of BCR-AS was the most effective inhibitor of $p210^{bcr-abl}$ in vitro compared to phosphodiester of phosphorothioate capped ODNs. To determine whether such properties are important in cellular assays, K562 cells were electroporated in the presence of BCR-AS with various backbone modifications, and one hour later phosphotyrosine content was assessed by Western analysis (FIG. 7A). While the all-phosphorothioate species had no effect, the phosphodiester and phosphorothioate capped species were equally effective. FIG. 7B is a Western analysis of $p210^{bcr-abl}$ performed under the same conditions. It demonstrates that the changes in phosphotyrosine content are not due to changes in $p210^{bcr-abl}$ protein level.

EXAMPLE 7

ODN effects upon exogenous substrate phosphorylation

While the ability of $p210^{bcr-abl}$ to autophosphorylate itself in vitro correlates with effects in the cell, data are now emerging to suggest that the ability of the kinase to bind to and to phosphorylate other proteins can be altered independently of effects on kinase autophosphorylation (32, 15). The $p210^{bcr-abl}$ kinase has been shown to be a major PTK in K562 cells, and anything that alters its substrate interactions would be expected to have significant effects upon overall cellular phosphotyrosine content (38, 39). The ability of BCR-AS to alter phosphorylation by $p210^{bcr-abl}$ of the exogenous substrate enolase was examined.

Figure 8:
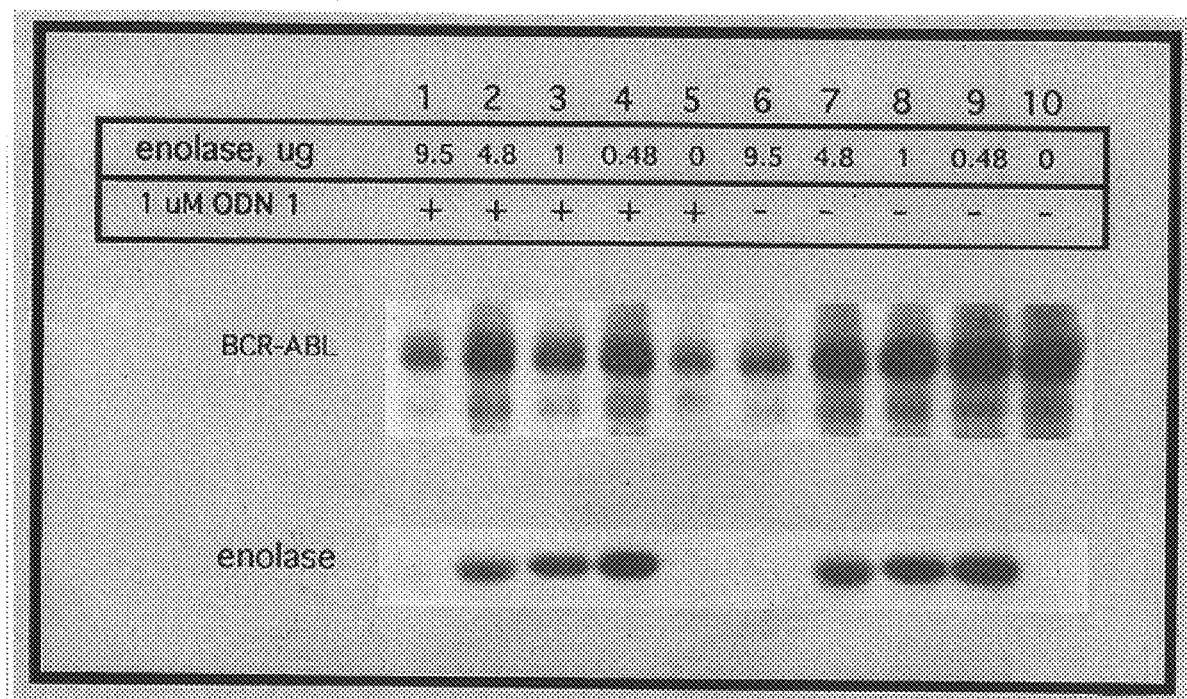
FIG. 8. Effect of BCR-AS upon $p210^{bcr-abl}$ kinase activity in the presence of enolase. One million K562 cells were immunoprecipitated and kinase reactions performed as described in Example 1. Reactions were run for three minutes with varying amounts of enolase in the presence or absence of 1 μM BCR-AS. Reaction products were visualized by autoradiography. Data are representative of three experiments.

$P210^{bcr-abl}$ from K562 cells was immunoprecipitated and kinase assays performed in the presence or absence of 1 µM BCR-AS with varying amounts of enolase present. The results can be seen in FIG. 8. While enolase appears to directly inhibit kinase activity at 9.5 ug per reaction (6 µM) irrespective of the presence of BCR-AS (see lanes 1 and 6), at lower concentrations of enolase, BCR-AS has only a slight effect upon autophosphorylation and no effect upon phosphorylation of enolase (see lanes 2–4 and 7–9). Even when BCR-AS is present at a 3.6:1 molar ratio compared to enolase, there is no significant inhibition of either auto- or substrate phosphorylation (compare lanes 4 and 9). Note that inhibition of autophosphorylation can be readily seen in the absence of enolase (see lanes 5 and 10).

EXAMPLE 8

ODN inhibition of $p210^{bcr-abl}$ inmunoprecipitation.

Figure 9A:
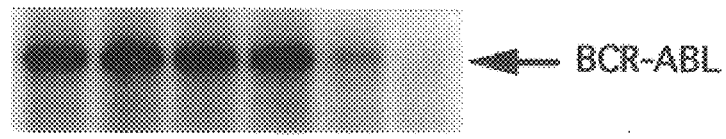
FIG. 9A. Interaction of T-21 ODN with $p210^{bcr-abl}$ (A) Immunoprecipitation-kinase assay of $p_{210}^{bcr-abl}$ from $1 \times 10^6$ K562 cells exposed to various concentrations of T-21 overnight as follows: lane 1, no ODN control; lane 2, 0.001 μM; lane 3, 0.01 μM; lane 4, 0.1 μM; lane 5, 1 μM; lane 6, 10 μM. Kinase assays were performed as described in Example 1.
Figure 9B:
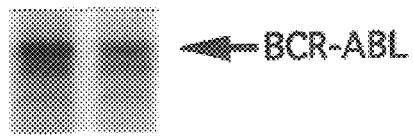
FIG. 9B. Effect of T-21 added directly to the kinase reaction. Immunoprecipitation-kinase assays were performed as in FIG. 9A except that T-21 was added directly to the kinase reaction; lane 1, no ODN control; lane 2, 1 AM T-21.
Figure 9C:
FIG. 9C. Inhibition of $p210^{bcr-abl}$ immunoprecipitation by T-21. Ten FM T-21 was added to the lysate from $1 \times 10^6$ K562 cells (lane 2) and $p210^{bcr-abl}$ immunoprecipitated with the BCR directed antibody, clone 7C6; no ODN was added to the lysate immunoprecipitated in lane 1. After extensive washing, the immunoprecipitates were separated on a 7% SDS polyacrylamide gel, transferred to nitrocellulose, and probed with an anti-phosphotyrosine antibody. Data are representative of at least two separate experiments.

In experiments designed to test the specificity of BCR-AS, an ODN composed solely of thymidylic acid residues (T-21) i.e., 5' TTTTTTTTTTTTTTTTTTTTT 3' (SEQ ID NO.: 12) was capable of interfering with $p210^{bcr-abl}$ immunoprecipitation. K562 cells, treated with various concentrations of T-21 overnight and then vigorously washed, demonstrate an apparent reduction of $p210^{bcr-abl}$ kinase activity, as determined by an immunoprecipitation in vitro kinase assay. From the data in FIG. 9A, one can calculate an $IC_{50}$ of less than 1 µM. If, however, $p210^{bcr-abl}$ is first immunoprecipitated and T-21 is then added to the kinase reaction at 1 µM, only moderate inhibition is seen (FIG. 9B). This apparent discrepancy appears to be due to the ability of T-21 to inhibit precipitation of $p210^{bcr-abl}$ by the BCR-directed antibody, clone 7C6. This conclusion was suggested by the data in FIG. 9C. Immunoprecipitation of $p210^{bcr-abl}$ from K562 cell lysates with clone 7C6 in the presence and absence of 10 µM T-21, followed by Western analysis for phosphotyrosine, reveals a nearly total inhibition of $p210^{bcr-abl}$ immunoprecipitation in the presence of T-21. Inhibition of $p210^{bcr-abl}$ immunoprecipitation was not seen with the other ODNs used in this study (data now shown).

EXAMPLE 9

Effects of oligodeoxynucleotides upon K562 cell growth

Figure 10:
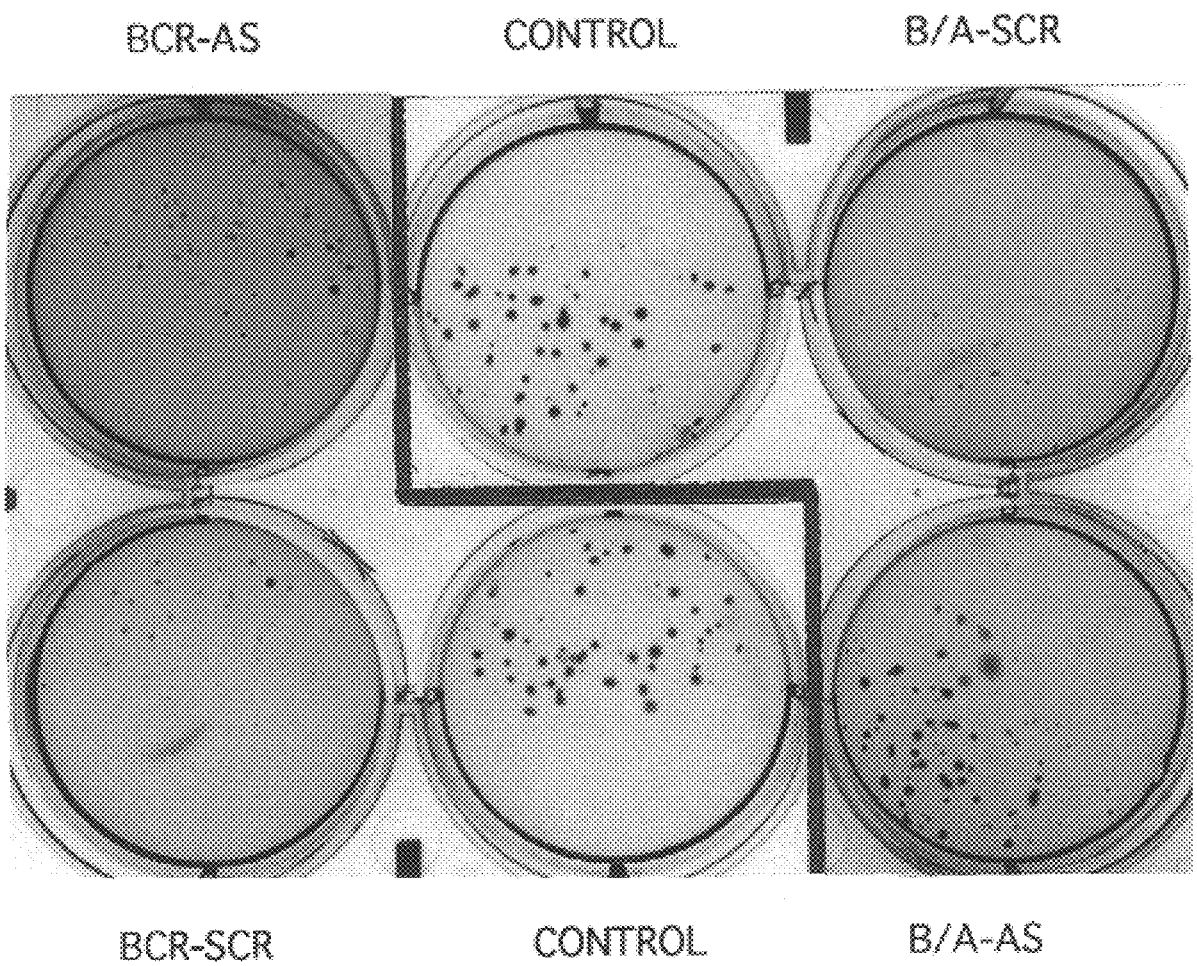
FIG. 10. ODNs inhibit growth of KS62 cells in soft agar. K562 cells were plated in soft agar as described in Example 9 at $2 \times 10^3$ cells/ml without ODN (control) or in the presence of 50 μM ODN and so maintained for two weeks. Similar results were obtained in a duplicate experiment.

To evaluate the effects of these various ODNs of K562 cell growth, both growth in liquid culture and growth in soft agar were examined. ODNs were chosen which either did (BCR-AS, BCR-SCR, B/A-SCR) or did not (B/A-AS) rapidly reduce protein phosphotyrosine content following electroporation. Cells were electroporated in the presence of 50 µM ODN and kept in liquid culture. For soft agar cloning experiments, cells were not electroporated, but were grown in the presence of 50 µM ODN for two weeks. Liquid cultures were replenished with fresh medium containing 50 µM ODN. Two weeks following incubation in liquid culture, the number of trypan blue-excluding cells was determined. No effect on cell growth in liquid culture could be observed with any ODN tested (data not shown). Contrary to these findings, those ODNs which reduced protein phosphotyrosine content following electroporation (BCR-AS, BCR-SCR, and B/A-SCR; see FIG. 5) also inhibited the ability of these cells to form colonies in soft agar, while the ODN which had no effect on cellular phosphotyrosine levels (B/A-AS) also failed to effect the cloning ability of the cells (FIG. 10).

REFERENCES

1. Hunter, T. (1991) *Methods Enzymol.* 200, 3–37.
2. Hunter, T. (199) *Curr. Opin. Cell Biol.* 1, 1168–1181.
3. Ullrich, A. and Schlessinger, J. (1990) *Cell* 61, 203–212.
4. Bolen, J. B. Viellette, A., Schwartz, A. M., DeSeau, V. and Rosen, N. (1987) *Proc. Natl. Acad. Sci. USA* 84, 2251–2255.
5. Di Marco, E., Pierce, J. H., Aaronson, S. A. and Di Fione, P. P. (1990) *Nat. Immun. Cell Growth Regulat.* 9, 209–221.
6. Gullick, W. J. (1991) *Brit. Med. Bull.* 47, 87–97.
7. Hunter, T. (1991) *Cell* 64, 249–270.
8. Druker, B. J., Mamon, B. S. and Roberts, T. M. (1989) *New Engl. J. Med.* 321, 1383–1391.
9. Hunter, T. and Sefton, B. M. (1980) *Proc. Natl. Acad. Sci. USA* 17, 1311–1315.
10. Tritton, T. R. and Hichman, M. A. (1990) *Cancer Cells* 2, 95–105.
11. Powis, G. (1991) *Trends Pharmacol. Sci.* 12, 188–194.
12. Yaish, P., Gazit, A., Gilon, C. and Levitzi, A. (1988) *Science* 242, 933–935.

13. Burke, T. R. (1992) *Drugs of the Future* 17, 119–131.

14. Kemp, B. E., Pearson, R. B., and House, C. M. (1991) *Method Enzymol.* 201, 287–303.

15. Konopka, J. B. and Witte, O. N. (1985) *Mol. Cell. Biol.* 5, 3116–3123.

16. Gishizky, M. L. and Witte, O. N. (1992) *Science* 256, 836–839.

17. Weber, W., Bertics, P. J. and Gill, G. N. (1984) *J. Biol. Chem.* 259, 14631–14636.

18. Kypta, R. M., Goldberg, Y., Ulug, E. T. and Courtneidge, S. A. (199)) *Cell* 62, 481–482.

19. Sartor, O., Sameshima, J. H. and Robbins, K. C. (1991) *J. Biol. Chem.* 266, 6462–6466.

20. Draetta, G. and Beach, D. (1989) *Cell* 54, 17–26.

21. Mayer, S. E., Stull, J. T., Wastila, W. B. and Thompson, B. (1974) *Methods Enzymol.* 38, 66–73.

22. Clark-Lewis, I., Sanghera, J. S. and Pelech, S. L. (1991) *J. Biol. Chem,* 266, 15180–15184.

23. Grosveld, G., Verwoerd, T., VanAgthoven, T., DeKlein, A., Ramachandran, K. L., Heisterkamp, N., Stam, D. and Groeffen, J. (1986) *Mol. Cell. Biol.* 6, 607–616.

24. Shtivelman, E., Lifshitz, B., Gale, R. P. and Canaani, E. (1985) *Nature (Lond.)*, 315, 550–554.

25. Konopka, J. B., Watanabe, S. M. and Witte, O. N. (1984) *Cell* 37, 1035–1042.

26. Maxwell, S. A., Kurzrock, R., Parsons. S. J., Talpaz, M., Gallick, G. E., Kloetzer, W. S. Arlinghaus, R. B., Kouttah, N. M. Keating, M. J. and Gutterman, J. U. (1987) *J. Cancer Res.* 47, 1731–1739.

27. Pendergast, A. M., Muller, A. J., Havlik, M. H., Maru, Y. and Witte, O. N. (1991) *Cell* 66, 161–171.

28. Hands, S. K. and Quinn, A. M. (1991) *Methods Enzymol.* 200, 38–61.

29. Mayer, B. J., Jackson, P. K. and Baltimore, D. (1991) *Biochemistry* 88, 627–631.

30. Koch, C. A., Anderson, D. Moran, M. G. Ellis, C. and Pawson, T. (1991) *Science* 252, 668–674.

31. Montminy, M. (1993) *Science* 261, 1694–1695.

32. Pendergast, A. M., Gishizky, M. L., Havlik, M. H. and Witte, O. N. (1993) *Mol. Cell. Biol.* 13, 1728–1736.

33. Bock, L. C., Griffin, L. C., Latham, J. A., Vermaas, E. H. and Toole, J. J. (1992) *Nature* 355, 564–566.

34. Stein, C. A. and Cheng, Y. C. (1993) *Science* 261, 1004–1112.

35. Tuerk, C., MacDougal S. and Gold, L (1992) *Proc. Natl. Acad. Sci. USA* 89, 6988–6992.

36. Gao, W., Hanes, R. N. Vazquez-Padua, M. A., Stein, C. A., Cohen, J. S. and Cheng, Y. (1990) *Antimicrobial Agents and Chemother.* 34, 808–812.

37. Marshall; W. S. and Caruthers, M. H. (1993) *Science* 259, 1564, 1570.

38. Alitalo, R. (1987). The bcr-abl tyrosine kinase activity is extinguished by TPA in K562 leukemia cells. *FEBS Letters* 222, 293–298.

39. Richardson, J. M., Morla, A. O. and Wang, J. Y. J. (1987). Reduction in protein tyrosine phosphorylation during differentiation of human leukemia cell line K-562. *Cancer Research* 47, 4066–4070.

40. Bergan, R., Connell, Y., Fahmy, B. and Neckers, L. (1993). Electroporation enhances c-myc antisense oligodeoxynucleotide efficacy. *Nucleic Acids Research* 21, 3567–3573.

41. Cohen, S. N. (1993). Bacterial plasmids: their extraordinary contribution to molecular genetics. *Gene* 135, 67–76.

42. Neckers, L., Whitesell, L., Rosolen, A. and Geselowitz, D. A. (1992). Antisense inhibition of oncogene expression. *Crit Rev Oncog* 3, 175–231.

43. Magrath, I. T. (1994). Prospects for the therapeutic use of antisense oligonucleotides in malignant lymphomas. *Ann. Oncol.* 5 (Suppl.), 567–570.

44. Schreier, H. (1994). The new frontier: gene and oligonucleotide therapy. *Pharm Acta Helv* 68, 145–159.

45. Skorski, T., Nieborowska-Skorska, M., Nicolaides, N. C., Szczylic, C., Iversen, P., Iozzo, R. V., Zon, G. and Calabretta, B. (1994). Suppression of Philadelphia leukemia cell growth in mice by BCR-ABL antisense oligodeoxynucleotide. *Proc Natl Acad Sci USA* 91, 4504–4508.

46. Bayever, E., Iversen, P. L. Bishop, M. R., Sharp, J. G., Tewary, H. K., Arneson, M. A. Pirruccello, S. J., Ruddon, R. W., Kessinger, A., Zon, G. and et al (1993). Systemic administration of a phosphorothioate oligonucleotide with a sequence complementary to p53 for acute myelogenous leukemia and myelodysplastic syndrome: initial results of a phase 1 trial. *Antisense Res Dev* 3, 383–390.

We claim:

1. A purified oligonucleotide comprising at least one sequence, which sequence is selected from the group consisting of: SEQ ID NO: 2, SEQ ID NO: 4, SEQ. ID NO: 6, SEQ ID NO: 7, and a modified sequence of SEQ ID No: 2, SEQ ID No: 4, SEQ ID No: 6 or SEQ ID No: 7 wherein the modified sequence contains at least one modified linking group, a modified sugar residue, a modified base or combinations thereof, wherein the modified base is selected from the group consisting of 5-fluorouracil, 5-bromouracil, 5-chlorouracil, 5-iodouracil, hypoxanthine, xanthine, 4-acetyl cytosine, 5-(carboxyhydroxylmethyl)uracil, 5-carboxymethylaminomethyl-2-thio-uridine, 5-carboxymethylaminomethyluracil, dihydrouracil, beta-D-galactosylqueosine, inosine, N6-isopentenyladenine, 1-methyladenine, 1-methylpseudouracil, 1-methylguanine, 1-methylinosine, 2,2-dimethylguanine, 2-methyladenine, 2-ethylguanine, 3-methylcytosine, 5-methylcytosine, N6-methyladenine, 7-methylguanine, 5-methylaminomethyluracil, 5-methoxyaminomethyl-2-thiorouracil, beta-D-mannosylqueosine, 5'-methoxycarbonylmethyluracil, 5-methoxyuracil, 2-methylthio-N6-isopentenyladenine, uracil-5-oxyacetic acid methyl ester, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid, 3(3-amino-3-N-2-carboxypropyl)uracil, and 2,6-diaminopurine wherein said purified pligonucleotide consists of at most about 100 nucleotides.

2. A purified oligonucleotide comprising a sequence which sequence is selected from the group consisting of SEQ ID NO: 2, SEQ ID NO: 4, SEQ ID NO: 6, and SEQ ID NO: 7 wherein said purified oligonucleotide consists of at most about 100 nucleotides.

3. A purified oligonucleotide consisting of a sequence selected from the group consisting of: SEQ ID NO: 1, SEQ ID NO: 3, SEQ ID NO: 5, SEQ ID NO: 11, and a modified sequence of SEQ ID No: 1, SEQ ID No: 3, SEQ ID No: 5, or SEQ ID No: 11 wherein the modified sequence contains at least one modified linking group, a modified sugar residue, a modified base or combinations thereof, wherein the modified base is selected from the group consisting of 5-fluorouracil, 5-bromouracil, 5-chlorouracil, 5-iodouracil, hypoxanthine, xanthine, 4-acetyl cytosine, 5-(carboxyhydroxylmethyl)uracil, 5-carboxymethylaminomethyl-2-thiouridine, 5-carboxymethylaminomethyluracil, dihydrouracil, beta-D-thiouridine, galactosylqueosine, inosine, N6-isopentenyladenine, 1-methyladenine, 1-methylpseudouracil, 1-methylguanine, 1-methylinosine, 2,2-dimethylguanine, 2-methyladenine, 2-ethylguanine, 3-methylcytosine, 5-methylcytosine, N6-methyladenine, 7-methylguanine, 5-methylaminomethyluracil, 5-methoxyaminomethyl-2-thiorouracil, beta-D-mannosylqueosine, 5'-methoxycarbonylmethyluracil, 5-methoxyuracil, 2-methylthio-N6-isopentenyladenine, uracil-5-oxyacetic acid methyl ester, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid, 3(3-amino-3-N-2-carboxypropyl)uracil, and 2,6-diaminopurine wherein said modified sequence containing at least one of said modified bases specifically binds to the same molecular target as is specifically bound by any of SEQ ID NO: 1, SEQ ID NO: 3, SEQ ID NO: 5, or SEQ ID NO: 11.

4. A purified oligonucleotide consisting of a sequence which sequence is selected from the group consisting of: SEQ ID NO: 1, SEQ ID NO: 3, SEQ ID NO: 5, and SEQ ID NO: 11.

5. The oligonucleotide according to claim 1 wherein the modified linking group is phosphorothioate.

6. The oligonucleotide according to claim 3 wherein the modified linking group is phosphorothioate.

7. The oligonucleotide according to claim 1 wherein the modified sugar has at least one hydroxyl group substituted by a halogen or an aliphatic group.

8. The oligonucleotide according to claim 3 wherein the modified sugar has at least one hydroxyl group substituted by a halogen or an aliphatic group.

9. The oligonucleotide according to claim 1 wherein the modified sugar is functionalized as an ether or amine.

10. The oligonucleotide according to claim 3 wherein the modified sugar is functionalized as an ether or amine.

11. A pharmaceutical composition for medical use comprising an oligonucleotide or mixture thereof of claims 1 through 9 or 10 and a physiologically acceptable excipient.

12. A composition for diagnostic use which comprises an oligonucleotide of claims 1 through 9 or 10 or mixture thereof.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 21 base pairs
      (B) TYPE: Nucleic acid
      (C) STRANDEDNESS: Single
      (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:1:

GTCCACCATG GCGCGGCCGG C                                                  21

(2) INFORMATION FOR SEQ ID NO:2:

(i) SEQUENCE CHARACTERISTICS:
              (A) LENGTH: 21 base pairs
              (B) TYPE: Nucleic acid
              (C) STRANDEDNESS: Single
              (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:2:

TCCGCGAACC CGGTGCGCCG G                                                  21

(2) INFORMATION FOR SEQ ID NO:3:

(i) SEQUENCE CHARACTERISTICS:
              (A) LENGTH: 21 base pairs
              (B) TYPE: Nucleic acid
              (C) STRANDEDNESS: Single
              (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:3:

TCCAGGCTGC TGCCCCATAA A                                                  21

(2) INFORMATION FOR SEQ ID NO:4:

(i) SEQUENCE CHARACTERISTICS:
              (A) LENGTH: 21 base pairs
              (B) TYPE: Nucleic acid
              (C) STRANDEDNESS: Single
              (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:4:

CCGACCACTT CCGAGTACTA G                                                  21

(2) INFORMATION FOR SEQ ID NO:5:

(i) SEQUENCE CHARACTERISTICS:
              (A) LENGTH: 21 base pairs
              (B) TYPE: Nucleic acid
              (C) STRANDEDNESS: Single
              (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:5:

CGCTGAAGTT TTGAACTCTG C                                                  21

-continued (2) INFORMATION FOR SEQ ID NO:6:

(i) SEQUENCE CHARACTERISTICS:
        (A) LENGTH: 21 base pairs
        (B) TYPE: Nucleic acid
        (C) STRANDEDNESS: Single
        (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:6:

TGTACGTCCG GCTTACTAGT A                                   21

(2) INFORMATION FOR SEQ ID NO:7:

(i) SEQUENCE CHARACTERISTICS:
        (A) LENGTH: 21 base pairs
        (B) TYPE: Nucleic acid
        (C) STRANDEDNESS: Single
        (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:7:

GGCGGCCGCG CTGCAACCCG T                                   21

(2) INFORMATION FOR SEQ ID NO:8:

(i) SEQUENCE CHARACTERISTICS:
        (A) LENGTH: 21 base pairs
        (B) TYPE: Nucleic acid
        (C) STRANDEDNESS: Single
        (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:8:

TGCCCAACGT CGCGCCGGCG G                                   21

(2) INFORMATION FOR SEQ ID NO:9:

(i) SEQUENCE CHARACTERISTICS:
        (A) LENGTH: 21 base pairs
        (B) TYPE: Nucleic acid
        (C) STRANDEDNESS: Single
        (D) TOPOLOGY: Linear (ii) MOLECULE TYPE: Other nucleic acid (iii) HYPOTHETICAL: Yes (iv) ANTI-SENSE: No (xi) SEQUENCE DESCRIPTION: SEQ ID NO:9:

GGCCGTGCAG CTCGCACCGG C                                   21

(2) INFORMATION FOR SEQ ID NO:10:

(i) SEQUENCE CHARACTERISTICS:

```
            (A) LENGTH:  21 base pairs
            (B) TYPE:  Nucleic acid
            (C) STRANDEDNESS:  Single
            (D) TOPOLOGY:  Linear (ii) MOLECULE TYPE:  Other nucleic acid (iii) HYPOTHETICAL:  Yes (iv) ANTI-SENSE:  No (xi) SEQUENCE DESCRIPTION: SEQ ID NO:10:

TCCGCGAACC CGGTGCGCCG G                                              21

(2) INFORMATION FOR SEQ ID NO:11:

(i) SEQUENCE CHARACTERISTICS:
            (A) LENGTH:  21 base pairs
            (B) TYPE:  Nucleic acid
            (C) STRANDEDNESS:  Single
            (D) TOPOLOGY:  Linear (ii) MOLECULE TYPE:  Other nucleic acid (iii) HYPOTHETICAL:  Yes (iv) ANTI-SENSE:  No (xi) SEQUENCE DESCRIPTION: SEQ ID NO:11:

GGCGGCGGCG GCGGCGGCGG C                                              21

(2) INFORMATION FOR SEQ ID NO:12:

(i) SEQUENCE CHARACTERISTICS:
            (A) LENGTH:  21 base pairs
            (B) TYPE:  Nucleic acid
            (C) STRANDEDNESS:  Single
            (D) TOPOLOGY:  Linear (ii) MOLECULE TYPE:  Other nucleic acid (iii) HYPOTHETICAL:  Yes (iv) ANTI-SENSE:  No (xi) SEQUENCE DESCRIPTION: SEQ ID NO:12:

TTTTTTTTTT TTTTTTTTTT T                                              21
```